(12) United States Patent
Nandy et al.

(10) Patent No.: US 7,935,347 B2
(45) Date of Patent: May 3, 2011

(54) DNA SEQUENCE, AND RECOMBINANT PREPARATION OF GROUP 4 MAJOR ALLERGENS FROM CEREALS

(75) Inventors: Andreas Nandy, Hamburg (DE); Helmut Fiebig, Schwarzenbeck (DE); Oliver Cromwell, Suesel-Fassendorf (DE)

(73) Assignee: Merck Patent GmbH, Darmstadt (DE)

( * ) Notice: Subject to any disclaimer, the term of this patent is extended or adjusted under 35 U.S.C. 154(b) by 353 days.

(21) Appl. No.: 10/583,089

(22) PCT Filed: Dec. 1, 2004

(86) PCT No.: PCT/EP2004/013664
§ 371 (c)(1),
(2), (4) Date: Jun. 15, 2006

(87) PCT Pub. No.: WO2005/059136
PCT Pub. Date: Jun. 30, 2005

(65) Prior Publication Data
US 2008/0108561 A1    May 8, 2008

(30) Foreign Application Priority Data
Dec. 16, 2003  (DE) .................................. 103 59 351

(51) Int. Cl.
*A61K 38/00* (2006.01)
*A61K 39/00* (2006.01)
*A61K 39/35* (2006.01)
*A61K 39/36* (2006.01)
*A01N 37/18* (2006.01)
*C07K 1/00* (2006.01)
*C07K 14/00* (2006.01)
*C07K 17/00* (2006.01)

(52) U.S. Cl. ....... 424/185.1; 424/275.1; 514/2; 530/350
(58) Field of Classification Search .................. None
See application file for complete search history.

(56) References Cited

U.S. PATENT DOCUMENTS
5,762,943 A * 6/1998 Dolovich et al. .......... 424/275.1
2005/0074464 A1    4/2005 Deweerd
2006/0177470 A1 * 8/2006 Fiebig et al. ............... 424/275.1

FOREIGN PATENT DOCUMENTS
WO   WO 03025009      3/2003
WO   WO 2004000881    12/2003

OTHER PUBLICATIONS

Tarzi et al. 'Peptide immunotherapy for allergic disease.'Expert Opin. Biol. Therap. 3(4):617-626, 2003.*
Gavrovic et al. 'Microheterogeneity examination of grass group 4 allergens.' Allergy 53(Suppl 43):27, 1998.*
Stumvoll S et al: "Purification, Structural and Immunological Chacateriaztion of a Timothy Grass (Phleium Pratense) Pollen Allergen, PHL P 4, With Cross-Reactive Potential" Biological Chemistry, Bd. 383, Nor. 9, Sep. 2002, XP002260346.
Astwood J D et al: "Cloning and Expression Pattern of HOR V 9, the Group 9 Pollen Isoallergen From Barley" Gene: An International Journal of Genese and Genomes,Elsevier Science Publishers, Barking, GB, Bd. 182, Nr. 1-2 Dec. 5, 1996, XP004071930.
Rihs H P et al: "Polymerase Chain Reaction Based CDNA Clonong of Wheat Profilin: A Potential Plant Allergen" International Archives of Allergy and Immunology, Bd. 105, Jan. 1994, XP000604627.
Fahlbusch B et al: Detection and Quantification of Group 4 Allergens in Grass Pollen Extracts Using Monoclonal Antibodies: Clinical and Experimental Allergy, Blackwell Scientific Publications, London, GB, Bd. 28, Nr. 7, Jul. 1998, XP002260345.
Database EMBL'Online! 19. Nov. 2004, AJ862830.
Database EMBL 19. Nov. 2004, AJ862831.
Database ENBL 19. Nov. 2004, AJ862834.
Database ENBL 19. Nov. 2004, AJ862832.
Database EMBL 19. Nov. 2004, AJ862833.

* cited by examiner

*Primary Examiner* — Nora M Rooney
(74) *Attorney, Agent, or Firm* — Millen, White, Zelano, Branigan, P.C.

(57) ABSTRACT

The invention relates to the preparation of DNA sequences of group 4 major allergens from cereals. The invention also includes fragments, novel combinations of partial sequences and point mutations with hypoallergenic effects. The recombinant DNA molecules and the derived polypeptides, fragments, novel combinations of partial sequences and variants can be used for therapy of pollen-allergy diseases. The proteins produced by recombination can be applied to in-vitro and in-vivo diagnosis of pollen allergies.

4 Claims, No Drawings

SEQUENCE LISTING

<160> NUMBER OF SEQ ID NOS: 44

<210> SEQ ID NO 1

```
<211> LENGTH: 1603
<212> TYPE: DNA
<213> ORGANISM: Secale cereale
<220> FEATURE:
<221> NAME/KEY: CDS
<222> LOCATION: (1)..(1557)

<400> SEQUENCE: 1 aac tat agg gcc ttc gcg ctg gcg ctc ctc ttc tgc gcc ttg tcc tgc      48
Asn Tyr Arg Ala Phe Ala Leu Ala Leu Leu Phe Cys Ala Leu Ser Cys
 1               5                  10                  15 caa gcc gcc gcg gcc gcc tac gcg ccc gtg cct gcc aag gcg gac ttc      96
Gln Ala Ala Ala Ala Ala Tyr Ala Pro Val Pro Ala Lys Ala Asp Phe
             20                  25                  30 ctc gga tgc ctc atg aag gag ata ccg gcc cgc ctc ctc tac gcc aag     144
Leu Gly Cys Leu Met Lys Glu Ile Pro Ala Arg Leu Leu Tyr Ala Lys
         35                  40                  45 agc tcg cct gac tac ccc acc gtg ctg gcg cag acc atc agg aac tcg     192
Ser Ser Pro Asp Tyr Pro Thr Val Leu Ala Gln Thr Ile Arg Asn Ser
 50                  55                  60 cgg tgg tcg tcg ccg cag aac gtg aag ccg atc tac atc atc acc ccc     240
Arg Trp Ser Ser Pro Gln Asn Val Lys Pro Ile Tyr Ile Ile Thr Pro
 65                  70                  75                  80 acc aac gcc tcg cac atc cag tcc gcg gtg gtg tgc ggc cgc cgg cac     288
Thr Asn Ala Ser His Ile Gln Ser Ala Val Val Cys Gly Arg Arg His
                 85                  90                  95 ggc atc cgc ctc cgc gtg cgg agc ggc ggc cac gac tac gag ggc ctg     336
Gly Ile Arg Leu Arg Val Arg Ser Gly Gly His Asp Tyr Glu Gly Leu
            100                 105                 110 tcg tac cgg tct gag aaa ccc gag acg ttc gcc gtc gtc gac ctc aac     384
Ser Tyr Arg Ser Glu Lys Pro Glu Thr Phe Ala Val Val Asp Leu Asn
        115                 120                 125 aag atg cgg gca gtg tcg gtc gac ggc tac gcc cgc acg gcg tgg gtc     432
Lys Met Arg Ala Val Ser Val Asp Gly Tyr Ala Arg Thr Ala Trp Val
    130                 135                 140 gaa tcc ggc gcg cag ctc ggc gag ctc tac tac gcg atc gcc aag aac     480
Glu Ser Gly Ala Gln Leu Gly Glu Leu Tyr Tyr Ala Ile Ala Lys Asn
145                 150                 155                 160 agc ccc gtg ctc gcg ttc ccg gct ggc gtc tgc ccg tcc atc ggc gtc     528
Ser Pro Val Leu Ala Phe Pro Ala Gly Val Cys Pro Ser Ile Gly Val
                165                 170                 175 ggc ggc aac ttc gca ggc ggc ggc ttt ggc atg ctg ctg cgc aag tac     576
Gly Gly Asn Phe Ala Gly Gly Gly Phe Gly Met Leu Leu Arg Lys Tyr
            180                 185                 190 ggc atc gcc gct gag aac gtc atc gac gtc aag gtg gtc gac ccc aac     624
Gly Ile Ala Ala Glu Asn Val Ile Asp Val Lys Val Val Asp Pro Asn
        195                 200                 205 ggc aag ctg ctc gac aag agc tcc atg agc gcg gac cac ttc tgg gcc     672
Gly Lys Leu Leu Asp Lys Ser Ser Met Ser Ala Asp His Phe Trp Ala
    210                 215                 220 gtt agg ggc ggc ggc gga gag agc ttt ggc atc gtc gtc tcg tgg cag     720
Val Arg Gly Gly Gly Gly Glu Ser Phe Gly Ile Val Val Ser Trp Gln
225                 230                 235                 240 gtg aag ctc ctg ccg gtg cct ccc acc gtg acc gtc ctc aag atc ccc     768
Val Lys Leu Leu Pro Val Pro Pro Thr Val Thr Val Leu Lys Ile Pro
                245                 250                 255 aag acg gtg caa gaa ggc gcc ata gac ctc gtc aac aag tgg cag ctg     816
Lys Thr Val Gln Glu Gly Ala Ile Asp Leu Val Asn Lys Trp Gln Leu
            260                 265                 270 gtc ggg ccg gca ctt ccc ggc gac ctc atg atc cgc atc atc ctt gcc     864
Val Gly Pro Ala Leu Pro Gly Asp Leu Met Ile Arg Ile Ile Leu Ala
        275                 280                 285
```

| | | | | | | | | | | | | | | | |
|---|---|---|---|---|---|---|---|---|---|---|---|---|---|---|---|
| ggg | aac | agc | gcg | acg | ttc | gag | gcc | atg | tac | ctg | ggc | acc | tgc | agt | acc | 912 |
| Gly | Asn | Ser | Ala | Thr | Phe | Glu | Ala | Met | Tyr | Leu | Gly | Thr | Cys | Ser | Thr | |
| | 290 | | | | 295 | | | | | 300 | | | | | | | ctg acg ccg ctg atg agc agc aaa ttc ccc gag ctt ggc atg aac ccc    960
Leu Thr Pro Leu Met Ser Ser Lys Phe Pro Glu Leu Gly Met Asn Pro
305                 310                 315                 320 tcg cac tgc aac gag atg tcc tgg atc aag tcc atc ccc ttc atc cac   1008
Ser His Cys Asn Glu Met Ser Trp Ile Lys Ser Ile Pro Phe Ile His
            325                 330                 335 ctc ggc aag cag aac ctc gac gac ctc ctc aac cgg aac aac acc ttc   1056
Leu Gly Lys Gln Asn Leu Asp Asp Leu Leu Asn Arg Asn Asn Thr Phe
        340                 345                 350 aaa cca ttc gcc gaa tac aag tcg gac tac gtg tac cag ccc ttc ccc   1104
Lys Pro Phe Ala Glu Tyr Lys Ser Asp Tyr Val Tyr Gln Pro Phe Pro
    355                 360                 365 aag ccc gtg tgg gag cag atc ttc ggc tgg ctt gtg aag ccc ggc gcg   1152
Lys Pro Val Trp Glu Gln Ile Phe Gly Trp Leu Val Lys Pro Gly Ala
370                 375                 380 ggg atc atg atc atg gac ccc tat ggc gcc acc atc agc gct acc ccc   1200
Gly Ile Met Ile Met Asp Pro Tyr Gly Ala Thr Ile Ser Ala Thr Pro
385                 390                 395                 400 gaa gcg gcg acg ccg ttc cct cac cgc cag ggc gtc ctc ttc aac atc   1248
Glu Ala Ala Thr Pro Phe Pro His Arg Gln Gly Val Leu Phe Asn Ile
            405                 410                 415 cag tac gtc aac tac tgg ttc gct gag tca gcc ggc gcg gcg ccg ctg   1296
Gln Tyr Val Asn Tyr Trp Phe Ala Glu Ser Ala Gly Ala Ala Pro Leu
        420                 425                 430 cag tgg agc aag gac ata tac aag ttc atg gag ccg tac gtg agc aaa   1344
Gln Trp Ser Lys Asp Ile Tyr Lys Phe Met Glu Pro Tyr Val Ser Lys
    435                 440                 445 aat ccc agg cag gcg tat gcc aac tac agg gac atc gac ctt ggc agg   1392
Asn Pro Arg Gln Ala Tyr Ala Asn Tyr Arg Asp Ile Asp Leu Gly Arg
450                 455                 460 aat gag gtg gtg aac gac atc tcc acc tac agc agc ggc aaa gtg tgg   1440
Asn Glu Val Val Asn Asp Ile Ser Thr Tyr Ser Ser Gly Lys Val Trp
465                 470                 475                 480 ggt gag aag tac ttc aag ggc aac ttc caa agg ctc gcc att acc aag   1488
Gly Glu Lys Tyr Phe Lys Gly Asn Phe Gln Arg Leu Ala Ile Thr Lys
            485                 490                 495 ggc aag gtg gat cct cag gac tac ttc agg aac gag cag agc atc ccg   1536
Gly Lys Val Asp Pro Gln Asp Tyr Phe Arg Asn Glu Gln Ser Ile Pro
        500                 505                 510 cca ctg gtc gag aag tac tga tcgaggacct tgcatggaaa tttagtgcgt      1587
Pro Leu Val Glu Lys Tyr
    515 ggttggcgtt tcacat                                                 1603

<210> SEQ ID NO 2
<211> LENGTH: 518
<212> TYPE: PRT
<213> ORGANISM: Secale cereale

<400> SEQUENCE: 2

Asn Tyr Arg Ala Phe Ala Leu Ala Leu Leu Phe Cys Ala Leu Ser Cys
 1               5                  10                  15

Gln Ala Ala Ala Ala Tyr Ala Pro Val Pro Ala Lys Ala Asp Phe
            20                  25                  30

Leu Gly Cys Leu Met Lys Glu Ile Pro Ala Arg Leu Leu Tyr Ala Lys
        35                  40                  45

```
Ser Ser Pro Asp Tyr Pro Thr Val Leu Ala Gln Thr Ile Arg Asn Ser
 50                  55                  60

Arg Trp Ser Ser Pro Gln Asn Val Lys Pro Ile Tyr Ile Ile Thr Pro
 65                  70                  75                  80

Thr Asn Ala Ser His Ile Gln Ser Ala Val Val Cys Gly Arg Arg His
                 85                  90                  95

Gly Ile Arg Leu Arg Val Arg Ser Gly Gly His Asp Tyr Glu Gly Leu
            100                 105                 110

Ser Tyr Arg Ser Glu Lys Pro Glu Thr Phe Ala Val Val Asp Leu Asn
            115                 120                 125

Lys Met Arg Ala Val Ser Val Asp Gly Tyr Ala Arg Thr Ala Trp Val
130                 135                 140

Glu Ser Gly Ala Gln Leu Gly Glu Leu Tyr Tyr Ala Ile Ala Lys Asn
145                 150                 155                 160

Ser Pro Val Leu Ala Phe Pro Ala Gly Val Cys Pro Ser Ile Gly Val
                165                 170                 175

Gly Gly Asn Phe Ala Gly Gly Gly Phe Gly Met Leu Leu Arg Lys Tyr
            180                 185                 190

Gly Ile Ala Ala Glu Asn Val Ile Asp Val Lys Val Val Asp Pro Asn
            195                 200                 205

Gly Lys Leu Leu Asp Lys Ser Ser Met Ser Ala Asp His Phe Trp Ala
210                 215                 220

Val Arg Gly Gly Gly Gly Glu Ser Phe Gly Ile Val Val Ser Trp Gln
225                 230                 235                 240

Val Lys Leu Leu Pro Val Pro Pro Thr Val Thr Val Leu Lys Ile Pro
                245                 250                 255

Lys Thr Val Gln Glu Gly Ala Ile Asp Leu Val Asn Lys Trp Gln Leu
            260                 265                 270

Val Gly Pro Ala Leu Pro Gly Asp Leu Met Ile Arg Ile Ile Leu Ala
            275                 280                 285

Gly Asn Ser Ala Thr Phe Glu Ala Met Tyr Leu Gly Thr Cys Ser Thr
290                 295                 300

Leu Thr Pro Leu Met Ser Ser Lys Phe Pro Glu Leu Gly Met Asn Pro
305                 310                 315                 320

Ser His Cys Asn Glu Met Ser Trp Ile Lys Ser Ile Pro Phe Ile His
                325                 330                 335

Leu Gly Lys Gln Asn Leu Asp Asp Leu Leu Asn Arg Asn Asn Thr Phe
            340                 345                 350

Lys Pro Phe Ala Glu Tyr Lys Ser Asp Tyr Val Tyr Gln Pro Phe Pro
            355                 360                 365

Lys Pro Val Trp Glu Gln Ile Phe Gly Trp Leu Val Lys Pro Gly Ala
            370                 375                 380

Gly Ile Met Ile Met Asp Pro Tyr Gly Ala Thr Ile Ser Ala Thr Pro
385                 390                 395                 400

Glu Ala Ala Thr Pro Phe Pro His Arg Gln Gly Val Leu Phe Asn Ile
                405                 410                 415

Gln Tyr Val Asn Tyr Trp Phe Ala Glu Ser Ala Gly Ala Ala Pro Leu
            420                 425                 430

Gln Trp Ser Lys Asp Ile Tyr Lys Phe Met Glu Pro Tyr Val Ser Lys
            435                 440                 445

Asn Pro Arg Gln Ala Tyr Ala Asn Tyr Arg Asp Ile Asp Leu Gly Arg
            450                 455                 460

Asn Glu Val Val Asn Asp Ile Ser Thr Tyr Ser Ser Gly Lys Val Trp
465                 470                 475                 480
```

```
Gly Glu Lys Tyr Phe Lys Gly Asn Phe Gln Arg Leu Ala Ile Thr Lys
                485                 490                 495
Gly Lys Val Asp Pro Gln Asp Tyr Phe Arg Asn Glu Gln Ser Ile Pro
            500                 505                 510
Pro Leu Val Glu Lys Tyr
        515

<210> SEQ ID NO 3
<211> LENGTH: 1644
<212> TYPE: DNA
<213> ORGANISM: Secale cereale
<220> FEATURE:
<221> NAME/KEY: CDS
<222> LOCATION: (1)..(1563)

<400> SEQUENCE: 3
```

| | | | | | | | | | | | | | | | | |
|---|---|---|---|---|---|---|---|---|---|---|---|---|---|---|---|---|
| aac | tcg | agg | gcc | ttt | gct | ctg | gtg | ccc | ctc | ctc | atc | tgc | gtc | ttg | tcc | 48 |
| Asn | Ser | Arg | Ala | Phe | Ala | Leu | Val | Pro | Leu | Leu | Ile | Cys | Val | Leu | Ser | |
| 1 | | | 5 | | | | | 10 | | | | | 15 | | | |
| tgc | cac | gcc | gcc | gtc | tcc | tac | gcg | gcg | gcg | ccg | gtg | ccg | gcc | aag | gag | 96 |
| Cys | His | Ala | Ala | Val | Ser | Tyr | Ala | Ala | Ala | Pro | Val | Pro | Ala | Lys | Glu | |
| | | | 20 | | | | | 25 | | | | | 30 | | | |
| gac | ttc | ttc | gga | tgc | ctg | gtg | aag | gag | ata | ccg | gcc | cgc | ctc | ctc | tac | 144 |
| Asp | Phe | Phe | Gly | Cys | Leu | Val | Lys | Glu | Ile | Pro | Ala | Arg | Leu | Leu | Tyr | |
| | | 35 | | | | | 40 | | | | | 45 | | | | |
| gcc | aag | agc | tcg | cct | gcc | ttc | ccc | acc | gtc | ctg | gcg | cag | acc | atc | agg | 192 |
| Ala | Lys | Ser | Ser | Pro | Ala | Phe | Pro | Thr | Val | Leu | Ala | Gln | Thr | Ile | Arg | |
| | 50 | | | | | 55 | | | | | 60 | | | | | |
| aac | tcg | cgg | tgg | tcg | tcg | ccg | cag | agc | gtg | aag | ccg | ctc | tac | atc | atc | 240 |
| Asn | Ser | Arg | Trp | Ser | Ser | Pro | Gln | Ser | Val | Lys | Pro | Leu | Tyr | Ile | Ile | |
| 65 | | | | | 70 | | | | | 75 | | | | | 80 | |
| acc | ccc | acc | aac | gcc | tcc | cac | atc | cag | tcc | gcg | gtg | gtg | tgc | ggc | cgc | 288 |
| Thr | Pro | Thr | Asn | Ala | Ser | His | Ile | Gln | Ser | Ala | Val | Val | Cys | Gly | Arg | |
| | | | | 85 | | | | | 90 | | | | | 95 | | |
| cgg | cac | ggc | gtc | cgc | atc | cgc | gtg | cgg | agc | ggc | ggc | cac | gac | tac | gag | 336 |
| Arg | His | Gly | Val | Arg | Ile | Arg | Val | Arg | Ser | Gly | Gly | His | Asp | Tyr | Glu | |
| | | | 100 | | | | | 105 | | | | | 110 | | | |
| ggc | ctg | tcg | tac | cgg | tcc | gag | cgc | ccc | gag | gcg | ttc | gcc | gtc | gtc | gac | 384 |
| Gly | Leu | Ser | Tyr | Arg | Ser | Glu | Arg | Pro | Glu | Ala | Phe | Ala | Val | Val | Asp | |
| | | 115 | | | | | 120 | | | | | 125 | | | | |
| ctc | aac | aag | atg | cgg | gcc | gtg | gtg | gtc | gac | ggc | aag | gct | cgc | acg | gcg | 432 |
| Leu | Asn | Lys | Met | Arg | Ala | Val | Val | Val | Asp | Gly | Lys | Ala | Arg | Thr | Ala | |
| | 130 | | | | | 135 | | | | | 140 | | | | | |
| tgg | gtg | gac | tcc | ggt | gcg | cag | ctc | ggc | gag | ctc | tac | tac | gcc | atc | gcc | 480 |
| Trp | Val | Asp | Ser | Gly | Ala | Gln | Leu | Gly | Glu | Leu | Tyr | Tyr | Ala | Ile | Ala | |
| 145 | | | | | 150 | | | | | 155 | | | | | 160 | |
| aag | aac | agc | ccc | gtg | ctc | gcg | ttc | ccg | gcc | ggc | gtt | tgc | ccg | acc | att | 528 |
| Lys | Asn | Ser | Pro | Val | Leu | Ala | Phe | Pro | Ala | Gly | Val | Cys | Pro | Thr | Ile | |
| | | | | 165 | | | | | 170 | | | | | 175 | | |
| ggt | gta | ggc | ggc | aac | ttc | gct | ggc | ggc | ggc | ttc | ggc | atg | ctg | ctg | cgc | 576 |
| Gly | Val | Gly | Gly | Asn | Phe | Ala | Gly | Gly | Gly | Phe | Gly | Met | Leu | Leu | Arg | |
| | | | 180 | | | | | 185 | | | | | 190 | | | |
| aag | tac | ggc | atc | gcc | gcc | gag | aac | gtc | atc | gac | gtg | aag | gtg | gtc | gac | 624 |
| Lys | Tyr | Gly | Ile | Ala | Ala | Glu | Asn | Val | Ile | Asp | Val | Lys | Val | Val | Asp | |
| | | 195 | | | | | 200 | | | | | 205 | | | | |
| gcc | aac | ggc | aca | ctg | ctc | gac | aag | agc | tcc | atg | agc | gcg | gat | cac | ttc | 672 |
| Ala | Asn | Gly | Thr | Leu | Leu | Asp | Lys | Ser | Ser | Met | Ser | Ala | Asp | His | Phe | |
| | 210 | | | | | 215 | | | | | 220 | | | | | |
| tgg | gcc | gtc | agg | ggc | ggc | ggc | gga | gag | agc | ttc | ggc | atc | gtc | gtg | tcg | 720 |
| Trp | Ala | Val | Arg | Gly | Gly | Gly | Gly | Glu | Ser | Phe | Gly | Ile | Val | Val | Ser | |
| 225 | | | | | 230 | | | | | 235 | | | | | 240 | |

```
tgg cag gtg aag ctc ctc ccg gtg cct ccc acc gtg acc gtc ttc aag      768
Trp Gln Val Lys Leu Leu Pro Val Pro Pro Thr Val Thr Val Phe Lys
            245                 250                 255 atc ccc aag acg gtg caa gaa ggc gcc gta gag ctc atc aac aag tgg      816
Ile Pro Lys Thr Val Gln Glu Gly Ala Val Glu Leu Ile Asn Lys Trp
            260                 265                 270 cag cta gtc gcg ccg gcc ctc ccc gac gac ctg atg atc cgc atc atc      864
Gln Leu Val Ala Pro Ala Leu Pro Asp Asp Leu Met Ile Arg Ile Ile
            275                 280                 285 gct ttc ggc ggc acc gcc aag ttc gag gcc atg tac ctg ggc acc tgc      912
Ala Phe Gly Gly Thr Ala Lys Phe Glu Ala Met Tyr Leu Gly Thr Cys
        290                 295                 300 aaa gcc ctg aca ccg ctg atg agc agc aga ttc ccc gag ctc ggc atg      960
Lys Ala Leu Thr Pro Leu Met Ser Ser Arg Phe Pro Glu Leu Gly Met
305                 310                 315                 320 aac gcc tcg cac tgc aac gag atg ccc tgg atc aag tcc gtc cca ttc     1008
Asn Ala Ser His Cys Asn Glu Met Pro Trp Ile Lys Ser Val Pro Phe
                325                 330                 335 atc cac ctt ggc aag cag gcc acc ctc tcc gac ctc ctc aac cgg aac     1056
Ile His Leu Gly Lys Gln Ala Thr Leu Ser Asp Leu Leu Asn Arg Asn
            340                 345                 350 aac acc ttc aaa ccc ttc gcc gag tac aag tcg gac tac gtc tac cag     1104
Asn Thr Phe Lys Pro Phe Ala Glu Tyr Lys Ser Asp Tyr Val Tyr Gln
            355                 360                 365 ccc gtc ccc aag ccc gtc tgg gcg cag atc ttc gtc tgg ctc gtc aaa     1152
Pro Val Pro Lys Pro Val Trp Ala Gln Ile Phe Val Trp Leu Val Lys
            370                 375                 380 ccc ggc gcc ggg atc atg gtc atg gac ccc tac ggc gcc gcc atc agc     1200
Pro Gly Ala Gly Ile Met Val Met Asp Pro Tyr Gly Ala Ala Ile Ser
385                 390                 395                 400 gcc acc ccc gaa gcc gcc acg ccg ttc cct cac cgc aag gac gtc ctc     1248
Ala Thr Pro Glu Ala Ala Thr Pro Phe Pro His Arg Lys Asp Val Leu
                405                 410                 415 ttc aac atc cag tac gtc aac tac tgg ttc gac gag gca ggc ggc gcc     1296
Phe Asn Ile Gln Tyr Val Asn Tyr Trp Phe Asp Glu Ala Gly Gly Ala
            420                 425                 430 gcg ccg ctg cag tgg agc aag gac atg tac agg ttc atg gag ccg tac     1344
Ala Pro Leu Gln Trp Ser Lys Asp Met Tyr Arg Phe Met Glu Pro Tyr
            435                 440                 445 gtc agc aag aac ccc aga cag gcc tac gcc aac tac agg gac atc gac     1392
Val Ser Lys Asn Pro Arg Gln Ala Tyr Ala Asn Tyr Arg Asp Ile Asp
            450                 455                 460 ctc ggc agg aac gag gtg gtc aac gac atc tcc acc tat gcc agc ggc     1440
Leu Gly Arg Asn Glu Val Val Asn Asp Ile Ser Thr Tyr Ala Ser Gly
465                 470                 475                 480 aag gtc tgg ggc gag aag tac ttc aag ggc aac ttc caa agg ctc gcc     1488
Lys Val Trp Gly Glu Lys Tyr Phe Lys Gly Asn Phe Gln Arg Leu Ala
                485                 490                 495 att acc aag ggc aag gtg gat cct cag gac tac ttc agg aac gag cag     1536
Ile Thr Lys Gly Lys Val Asp Pro Gln Asp Tyr Phe Arg Asn Glu Gln
            500                 505                 510 agc atc ccg ccg ctg cta ggg aag tag tagtactctt gcttgcatgg           1583
Ser Ile Pro Pro Leu Leu Gly Lys
            515                 520 agatttgtag tgcgtctttc gcgtttcaaa tgcccaacta gtagaataag gatcgtgcgt   1643
a                                                                  1644

<210> SEQ ID NO 4
<211> LENGTH: 520
```

<212> TYPE: PRT
<213> ORGANISM: Secale cereale

<400> SEQUENCE: 4

```
Asn Ser Arg Ala Phe Ala Leu Val Pro Leu Leu Ile Cys Val Leu Ser
 1               5                  10                  15
Cys His Ala Ala Val Ser Tyr Ala Ala Ala Pro Val Pro Ala Lys Glu
             20                  25                  30
Asp Phe Phe Gly Cys Leu Val Lys Glu Ile Pro Ala Arg Leu Leu Tyr
         35                  40                  45
Ala Lys Ser Ser Pro Ala Phe Pro Thr Val Leu Ala Gln Thr Ile Arg
     50                  55                  60
Asn Ser Arg Trp Ser Ser Pro Gln Ser Val Lys Pro Leu Tyr Ile Ile
 65                  70                  75                  80
Thr Pro Thr Asn Ala Ser His Ile Gln Ser Ala Val Val Cys Gly Arg
                 85                  90                  95
Arg His Gly Val Arg Ile Arg Val Arg Ser Gly Gly His Asp Tyr Glu
            100                 105                 110
Gly Leu Ser Tyr Arg Ser Glu Arg Pro Glu Ala Phe Ala Val Val Asp
        115                 120                 125
Leu Asn Lys Met Arg Ala Val Val Asp Gly Lys Ala Arg Thr Ala
    130                 135                 140
Trp Val Asp Ser Gly Ala Gln Leu Gly Glu Leu Tyr Ala Ile Ala
145                 150                 155                 160
Lys Asn Ser Pro Val Leu Ala Phe Pro Ala Gly Val Cys Pro Thr Ile
                165                 170                 175
Gly Val Gly Gly Asn Phe Ala Gly Gly Phe Gly Met Leu Leu Arg
            180                 185                 190
Lys Tyr Gly Ile Ala Ala Glu Asn Val Ile Asp Val Lys Val Val Asp
        195                 200                 205
Ala Asn Gly Thr Leu Leu Asp Lys Ser Ser Met Ser Ala Asp His Phe
    210                 215                 220
Trp Ala Val Arg Gly Gly Gly Glu Ser Phe Gly Ile Val Val Ser
225                 230                 235                 240
Trp Gln Val Lys Leu Leu Pro Val Pro Pro Thr Val Thr Val Phe Lys
                245                 250                 255
Ile Pro Lys Thr Val Gln Glu Gly Ala Val Glu Leu Ile Asn Lys Trp
            260                 265                 270
Gln Leu Val Ala Pro Ala Leu Pro Asp Asp Leu Met Ile Arg Ile Ile
        275                 280                 285
Ala Phe Gly Gly Thr Ala Lys Phe Glu Ala Met Tyr Leu Gly Thr Cys
    290                 295                 300
Lys Ala Leu Thr Pro Leu Met Ser Ser Arg Phe Pro Glu Leu Gly Met
305                 310                 315                 320
Asn Ala Ser His Cys Asn Glu Met Pro Trp Ile Lys Ser Val Pro Phe
                325                 330                 335
Ile His Leu Gly Lys Gln Ala Thr Leu Ser Asp Leu Leu Asn Arg Asn
            340                 345                 350
Asn Thr Phe Lys Pro Phe Ala Glu Tyr Lys Ser Asp Tyr Val Tyr Gln
        355                 360                 365
Pro Val Pro Lys Pro Val Trp Ala Gln Ile Phe Val Trp Leu Val Lys
    370                 375                 380
Pro Gly Ala Gly Ile Met Val Met Asp Pro Tyr Gly Ala Ala Ile Ser
385                 390                 395                 400
```

-continued

```
Ala Thr Pro Glu Ala Ala Thr Pro Phe Pro His Arg Lys Asp Val Leu
            405                 410                 415

Phe Asn Ile Gln Tyr Val Asn Tyr Trp Phe Asp Glu Ala Gly Gly Ala
        420                 425                 430

Ala Pro Leu Gln Trp Ser Lys Asp Met Tyr Arg Phe Met Glu Pro Tyr
            435                 440                 445

Val Ser Lys Asn Pro Arg Gln Ala Tyr Ala Asn Tyr Arg Asp Ile Asp
    450                 455                 460

Leu Gly Arg Asn Glu Val Val Asn Asp Ile Ser Thr Tyr Ala Ser Gly
465                 470                 475                 480

Lys Val Trp Gly Glu Lys Tyr Phe Lys Gly Asn Phe Gln Arg Leu Ala
                485                 490                 495

Ile Thr Lys Gly Lys Val Asp Pro Gln Asp Tyr Phe Arg Asn Glu Gln
            500                 505                 510

Ser Ile Pro Pro Leu Leu Gly Lys
            515                 520

<210> SEQ ID NO 5
<211> LENGTH: 1608
<212> TYPE: DNA
<213> ORGANISM: Hordeum vulgare
<220> FEATURE:
<221> NAME/KEY: CDS
<222> LOCATION: (1)..(1557)

<400> SEQUENCE: 5 agc tcg agg gcc ttc gct ctg gtg ctc ctc ctc tgc gcc ttg tcc tgc      48
Ser Ser Arg Ala Phe Ala Leu Val Leu Leu Leu Cys Ala Leu Ser Cys
1               5                   10                  15 cac cac gct gcc gtc tcc tcc gcg cag gtg ccg gcc aag gac gac ttc      96
His His Ala Ala Val Ser Ser Ala Gln Val Pro Ala Lys Asp Asp Phe
                20                  25                  30 ctg gga tgc ctc gtg aag gag ata ccg gcc cgc ctc ctc ttc gcc aag     144
Leu Gly Cys Leu Val Lys Glu Ile Pro Ala Arg Leu Leu Phe Ala Lys
            35                  40                  45 agc tcg cct gcc ttc ccc gcc gtc ctg gag cag acc atc agg aac tcg     192
Ser Ser Pro Ala Phe Pro Ala Val Leu Glu Gln Thr Ile Arg Asn Ser
        50                  55                  60 cgg tgg tcg tcg ccg cag aac gtg aag ccg ctc tac atc atc acc ccc     240
Arg Trp Ser Ser Pro Gln Asn Val Lys Pro Leu Tyr Ile Ile Thr Pro
65                  70                  75                  80 acc aac acc tcc cac atc cag tct gct gtg gtg tgc ggc cgc cgg cac     288
Thr Asn Thr Ser His Ile Gln Ser Ala Val Val Cys Gly Arg Arg His
                85                  90                  95 ggc gtc cgc ctc cgc gtg cgg agc ggc ggc cac gac tac gag ggc ctg     336
Gly Val Arg Leu Arg Val Arg Ser Gly Gly His Asp Tyr Glu Gly Leu
            100                 105                 110 tcg tac cgg tcc gag cgc ccc gag gcg ttc gcc gtc gta gac ctc aac     384
Ser Tyr Arg Ser Glu Arg Pro Glu Ala Phe Ala Val Val Asp Leu Asn
        115                 120                 125 aag atg cgg acc gtg ttg gtc aac gaa aag gcc cgc acg gcg tgg gtg     432
Lys Met Arg Thr Val Leu Val Asn Glu Lys Ala Arg Thr Ala Trp Val
    130                 135                 140 gac tcc ggc gcg cag ctc ggc gag ctc tac tac gcc atc gcc aag aac     480
Asp Ser Gly Ala Gln Leu Gly Glu Leu Tyr Tyr Ala Ile Ala Lys Asn
145                 150                 155                 160 agc ccc gtg ctc gcg ttc cca gcc ggc gtt tgc ccg tcc att ggt gta     528
Ser Pro Val Leu Ala Phe Pro Ala Gly Val Cys Pro Ser Ile Gly Val
                165                 170                 175 ggt ggc aac ttc gct ggc ggc ggc ttc ggc atg ctg ctg cgc aag tac     576
```

```
Gly Gly Asn Phe Ala Gly Gly Phe Gly Met Leu Leu Arg Lys Tyr
            180                 185                 190 ggc atc gcc gcc gag aac gtc atc gac gtc aag ctg gtc gac gcc aac    624
Gly Ile Ala Ala Glu Asn Val Ile Asp Val Lys Leu Val Asp Ala Asn
        195                 200                 205 ggc aag ctg ctc gac aag agc tcc atg agc ccg gac cac ttc tgg gcc    672
Gly Lys Leu Leu Asp Lys Ser Ser Met Ser Pro Asp His Phe Trp Ala
    210                 215                 220 gtc agg ggc ggc ggc gga gag agc ttc ggc atc gtc gtc tcg tgg cag    720
Val Arg Gly Gly Gly Gly Glu Ser Phe Gly Ile Val Val Ser Trp Gln
225                 230                 235                 240 gtg aag ctt ctc ccg gtg cct ccc acc gtg act gtg ttt cag atc ccc    768
Val Lys Leu Leu Pro Val Pro Pro Thr Val Thr Val Phe Gln Ile Pro
                245                 250                 255 aag aca gtg caa gaa ggc gcc gta gac ctc atc aac aag tgg cag ctg    816
Lys Thr Val Gln Glu Gly Ala Val Asp Leu Ile Asn Lys Trp Gln Leu
            260                 265                 270 gtc gcg ccg gcc ctt ccc ggc gac atc atg atc cgc atc atc gcc atg    864
Val Ala Pro Ala Leu Pro Gly Asp Ile Met Ile Arg Ile Ile Ala Met
        275                 280                 285 ggg gac aaa gcg acg ttc gag gcc atg tac ctg ggc acc tgc aaa acc    912
Gly Asp Lys Ala Thr Phe Glu Ala Met Tyr Leu Gly Thr Cys Lys Thr
    290                 295                 300 ctg acg ccg ctg atg agc agc aaa ttc ccg gag ctt ggc atg aac ccc    960
Leu Thr Pro Leu Met Ser Ser Lys Phe Pro Glu Leu Gly Met Asn Pro
305                 310                 315                 320 tcg cac tgc aac gag atg ccc tgg atc aag tcc atc ccc ttc atc cac   1008
Ser His Cys Asn Glu Met Pro Trp Ile Lys Ser Ile Pro Phe Ile His
                325                 330                 335 ctt ggc aag cag gcc acc ctg gcc gac ctc ctc aac cgg aac aac acc   1056
Leu Gly Lys Gln Ala Thr Leu Ala Asp Leu Leu Asn Arg Asn Asn Thr
            340                 345                 350 ttc aaa ccc ttc gcc gaa tac aag tcg gac tac gtc tac cag ccc gtc   1104
Phe Lys Pro Phe Ala Glu Tyr Lys Ser Asp Tyr Val Tyr Gln Pro Val
        355                 360                 365 ccc aag ccc gtg tgg gag cag ctc ttc ggc tgg ctc acg aaa ccc ggc   1152
Pro Lys Pro Val Trp Glu Gln Leu Phe Gly Trp Leu Thr Lys Pro Gly
    370                 375                 380 gcg ggg atc atg gtc atg gac cca tac ggc gcc acc atc agc gcc acc   1200
Ala Gly Ile Met Val Met Asp Pro Tyr Gly Ala Thr Ile Ser Ala Thr
385                 390                 395                 400 ccc gaa gcg gcg acg ccg ttc cct cac cgc aag ggc gtc ctc ttc aac   1248
Pro Glu Ala Ala Thr Pro Phe Pro His Arg Lys Gly Val Leu Phe Asn
                405                 410                 415 atc cag tac gtc aac tac tgg ttc gcc gag gca gcc ggc gcc gcg ccg   1296
Ile Gln Tyr Val Asn Tyr Trp Phe Ala Glu Ala Ala Gly Ala Ala Pro
            420                 425                 430 ctg cag tgg agc aag gac att tac aaa ttc atg gag ccg ttc gtg agc   1344
Leu Gln Trp Ser Lys Asp Ile Tyr Lys Phe Met Glu Pro Phe Val Ser
        435                 440                 445 aag aac ccc agg cag gcg tac gcc aac tac agg gac atc gac ctc ggc   1392
Lys Asn Pro Arg Gln Ala Tyr Ala Asn Tyr Arg Asp Ile Asp Leu Gly
    450                 455                 460 agg aac gag gtg gtg aac gac atc tca acc tac agc agc ggc aag gtg   1440
Arg Asn Glu Val Val Asn Asp Ile Ser Thr Tyr Ser Ser Gly Lys Val
465                 470                 475                 480 tgg ggc gag aag tac ttc aag ggc aac ttc caa agg ctc gcc atc acc   1488
Trp Gly Glu Lys Tyr Phe Lys Gly Asn Phe Gln Arg Leu Ala Ile Thr
                485                 490                 495 aag ggc aag gtg gat ccc cag gac tac ttc agg aac gag cag agc atc   1536
```

```
Lys Gly Lys Val Asp Pro Gln Asp Tyr Phe Arg Asn Glu Gln Ser Ile
            500                 505                 510
```

```
ccg ccg ctg ctg ggc aag tag tgaccgagag tcttgcatgg agatttgtag      1587
Pro Pro Leu Leu Gly Lys
            515
```

```
tgcgtgcttg gcgtttctga t                                           1608
```

<210> SEQ ID NO 6
<211> LENGTH: 518
<212> TYPE: PRT
<213> ORGANISM: Hordeum vulgare

<400> SEQUENCE: 6

```
Ser Ser Arg Ala Phe Ala Leu Val Leu Leu Cys Ala Leu Ser Cys
1               5                   10                  15

His His Ala Ala Val Ser Ser Ala Gln Val Pro Ala Lys Asp Asp Phe
            20                  25                  30

Leu Gly Cys Leu Val Lys Glu Ile Pro Ala Arg Leu Leu Phe Ala Lys
            35                  40                      45

Ser Ser Pro Ala Phe Pro Ala Val Leu Glu Gln Thr Ile Arg Asn Ser
50                      55                      60

Arg Trp Ser Ser Pro Gln Asn Val Lys Pro Leu Tyr Ile Ile Thr Pro
65                  70                  75                  80

Thr Asn Thr Ser His Ile Gln Ser Ala Val Val Cys Gly Arg Arg His
                85                  90                      95

Gly Val Arg Leu Arg Val Arg Ser Gly Gly His Asp Tyr Glu Gly Leu
            100                 105                 110

Ser Tyr Arg Ser Glu Arg Pro Glu Ala Phe Ala Val Val Asp Leu Asn
            115                 120                 125

Lys Met Arg Thr Val Leu Val Asn Glu Lys Ala Arg Thr Ala Trp Val
130                 135                 140

Asp Ser Gly Ala Gln Leu Gly Glu Leu Tyr Tyr Ala Ile Ala Lys Asn
145                 150                 155                 160

Ser Pro Val Leu Ala Phe Pro Ala Gly Val Cys Pro Ser Ile Gly Val
                165                 170                 175

Gly Gly Asn Phe Ala Gly Gly Phe Gly Met Leu Leu Arg Lys Tyr
            180                 185                 190

Gly Ile Ala Ala Glu Asn Val Ile Asp Val Lys Leu Val Asp Ala Asn
            195                 200                 205

Gly Lys Leu Leu Asp Lys Ser Ser Met Ser Pro Asp His Phe Trp Ala
210                 215                 220

Val Arg Gly Gly Gly Gly Glu Ser Phe Gly Ile Val Val Ser Trp Gln
225                 230                 235                 240

Val Lys Leu Leu Pro Val Pro Pro Thr Val Thr Val Phe Gln Ile Pro
                245                 250                 255

Lys Thr Val Gln Glu Gly Ala Val Asp Leu Ile Asn Lys Trp Gln Leu
            260                 265                 270

Val Ala Pro Ala Leu Pro Gly Asp Ile Met Ile Arg Ile Ile Ala Met
            275                 280                 285

Gly Asp Lys Ala Thr Phe Glu Ala Met Tyr Leu Gly Thr Cys Lys Thr
290                 295                 300

Leu Thr Pro Leu Met Ser Ser Lys Phe Pro Glu Leu Gly Met Asn Pro
305                 310                 315                 320

Ser His Cys Asn Glu Met Pro Trp Ile Lys Ser Ile Pro Phe Ile His
                325                 330                 335
```

```
Leu Gly Lys Gln Ala Thr Leu Ala Asp Leu Leu Asn Arg Asn Asn Thr
        340                 345                 350

Phe Lys Pro Phe Ala Glu Tyr Lys Ser Asp Tyr Val Tyr Gln Pro Val
        355                 360                 365

Pro Lys Pro Val Trp Glu Gln Leu Phe Gly Trp Leu Thr Lys Pro Gly
        370                 375                 380

Ala Gly Ile Met Val Met Asp Pro Tyr Gly Ala Thr Ile Ser Ala Thr
385                 390                 395                 400

Pro Glu Ala Ala Thr Pro Phe Pro His Arg Lys Gly Val Leu Phe Asn
                405                 410                 415

Ile Gln Tyr Val Asn Tyr Trp Phe Ala Glu Ala Gly Ala Ala Pro
                420                 425                 430

Leu Gln Trp Ser Lys Asp Ile Tyr Lys Phe Met Glu Pro Phe Val Ser
        435                 440                 445

Lys Asn Pro Arg Gln Ala Tyr Ala Asn Tyr Arg Asp Ile Asp Leu Gly
        450                 455                 460

Arg Asn Glu Val Val Asn Asp Ile Ser Thr Tyr Ser Ser Gly Lys Val
465                 470                 475                 480

Trp Gly Glu Lys Tyr Phe Lys Gly Asn Phe Gln Arg Leu Ala Ile Thr
                485                 490                 495

Lys Gly Lys Val Asp Pro Gln Asp Tyr Phe Arg Asn Glu Gln Ser Ile
                500                 505                 510

Pro Pro Leu Leu Gly Lys
        515

<210> SEQ ID NO 7
<211> LENGTH: 1603
<212> TYPE: DNA
<213> ORGANISM: Triticum aestivum
<220> FEATURE:
<221> NAME/KEY: CDS
<222> LOCATION: (1)..(1557)

<400> SEQUENCE: 7 aac tat agg gcc ttc acg ctg gtg ctc ctc ttc tgc gcc ttg tcc tgt    48
Asn Tyr Arg Ala Phe Thr Leu Val Leu Leu Phe Cys Ala Leu Ser Cys
1               5                   10                  15 caa gcc gcc gcc acc tac gcg ccg gtg cct gcc aag gag gac ttc ctc    96
Gln Ala Ala Ala Thr Tyr Ala Pro Val Pro Ala Lys Glu Asp Phe Leu
            20                  25                  30 gga tgc ctc atg aag gag ata ccg gca cgc ctc ctc tac gcc aag agc   144
Gly Cys Leu Met Lys Glu Ile Pro Ala Arg Leu Leu Tyr Ala Lys Ser
        35                  40                  45 tcg cct gac ttc ccc acc gtc ctg gcg cag acc atc agg aac tcg cgg   192
Ser Pro Asp Phe Pro Thr Val Leu Ala Gln Thr Ile Arg Asn Ser Arg
    50                  55                  60 tgg ttg tcg ccg cag aac gtg aag ccg ctc tac atc atc acc ccc acc   240
Trp Leu Ser Pro Gln Asn Val Lys Pro Leu Tyr Ile Ile Thr Pro Thr
65                  70                  75                  80 aac gcc tcg cac atc cag tcc gcg gtg gtg tgc gga cgc cgg cac agc   288
Asn Ala Ser His Ile Gln Ser Ala Val Val Cys Gly Arg Arg His Ser
                85                  90                  95 gtc cgc ctc cgc gtc cgg agc ggc ggc cac gac tac gag ggc ctg tcg   336
Val Arg Leu Arg Val Arg Ser Gly Gly His Asp Tyr Glu Gly Leu Ser
            100                 105                 110 tac cgg tcc gag aaa ccc gag acg ttc gcc gtc gtc gac ctc aac aag   384
Tyr Arg Ser Glu Lys Pro Glu Thr Phe Ala Val Val Asp Leu Asn Lys
        115                 120                 125 atg cgg gca gtg ttg atc gac ggc tac gcc cgc acg gcg tgg gtc gaa   432
```

```
            Met Arg Ala Val Leu Ile Asp Gly Tyr Ala Arg Thr Ala Trp Val Glu
                130                 135                 140 tcc ggc gcg cag ctc ggc gag ctc tac tac gcc atc gcg aaa aac agc        480
Ser Gly Ala Gln Leu Gly Glu Leu Tyr Tyr Ala Ile Ala Lys Asn Ser
145                 150                 155                 160 ccc gtg ctc gcg ttc ccg gcc ggc gtc tgc ccg acc atc ggc gtc ggc        528
Pro Val Leu Ala Phe Pro Ala Gly Val Cys Pro Thr Ile Gly Val Gly
                165                 170                 175 ggc aac ttc gca ggc ggc ggc ttt ggc atg ctg ctg cgg aag tac ggc        576
Gly Asn Phe Ala Gly Gly Gly Phe Gly Met Leu Leu Arg Lys Tyr Gly
                180                 185                 190 atc gcc gcc gag aac gtc atc gac gtc aag gtg gtc gac ccc aac ggc        624
Ile Ala Ala Glu Asn Val Ile Asp Val Lys Val Val Asp Pro Asn Gly
                195                 200                 205 aag ctt ctc gac aag agc tcc atg agc ccg gac cac ttc tgg gcc gtc        672
Lys Leu Leu Asp Lys Ser Ser Met Ser Pro Asp His Phe Trp Ala Val
                210                 215                 220 agg ggc ggc ggc gga gag agc ttt ggc atc gtc gtg tcg tgg caa gtg        720
Arg Gly Gly Gly Gly Glu Ser Phe Gly Ile Val Val Ser Trp Gln Val
225                 230                 235                 240 aag ctc ctg ccg gtg cct ccc acc gtg acc gtg ttc aag atc ccc aag        768
Lys Leu Leu Pro Val Pro Pro Thr Val Thr Val Phe Lys Ile Pro Lys
                245                 250                 255 aca gtg caa gaa ggc gcc gta gac ctc gtc aac aag tgg caa ctg gtc        816
Thr Val Gln Glu Gly Ala Val Asp Leu Val Asn Lys Trp Gln Leu Val
                260                 265                 270 ggg ccg gcc ctt ccc ggc gac ctc atg atc cgc gtc atc gct gcg ggg        864
Gly Pro Ala Leu Pro Gly Asp Leu Met Ile Arg Val Ile Ala Ala Gly
                275                 280                 285 aac acc gcg aca ttc gag ggc atg tac ctg ggc acc tgc caa acc ctg        912
Asn Thr Ala Thr Phe Glu Gly Met Tyr Leu Gly Thr Cys Gln Thr Leu
                290                 295                 300 acg ccg ttg atg agc agc caa ttc ccc gag ctt ggc atg aac ccc tat        960
Thr Pro Leu Met Ser Ser Gln Phe Pro Glu Leu Gly Met Asn Pro Tyr
305                 310                 315                 320 cac tgc aac gag atg ccc tgg atc aag tcc atc ccc ttc atc cac ctc       1008
His Cys Asn Glu Met Pro Trp Ile Lys Ser Ile Pro Phe Ile His Leu
                325                 330                 335 ggc aaa gag gcc agc ctg gtc gac ctc ctc aac cgg aac aac acc ttc       1056
Gly Lys Glu Ala Ser Leu Val Asp Leu Leu Asn Arg Asn Asn Thr Phe
                340                 345                 350 aag ccc ttc gcc gaa tac aag tcg gac tac gtg tac cag ccc ttc ccc       1104
Lys Pro Phe Ala Glu Tyr Lys Ser Asp Tyr Val Tyr Gln Pro Phe Pro
                355                 360                 365 aag ccc gtg tgg gag cag atc ttc ggc tgg ctc acg aag ccc ggt ggg       1152
Lys Pro Val Trp Glu Gln Ile Phe Gly Trp Leu Thr Lys Pro Gly Gly
                370                 375                 380 ggg atg atg atc atg gac cca tac ggc gcc acc atc agc gcc acc ccc       1200
Gly Met Met Ile Met Asp Pro Tyr Gly Ala Thr Ile Ser Ala Thr Pro
385                 390                 395                 400 gaa gcg gcg acg ccg ttc cct cac cgc cag ggc gtt ctc ttc aac atc       1248
Glu Ala Ala Thr Pro Phe Pro His Arg Gln Gly Val Leu Phe Asn Ile
                405                 410                 415 cag tac gtc aac tac tgg ttc gcc gag gca gcc gcc gcg ccg ctg       1296
Gln Tyr Val Asn Tyr Trp Phe Ala Glu Ala Ala Ala Ala Pro Leu
                420                 425                 430 cag tgg agc aag gac atg tac aat ttc atg gag ccg tac gtg agc aag       1344
Gln Trp Ser Lys Asp Met Tyr Asn Phe Met Glu Pro Tyr Val Ser Lys
                435                 440                 445 aac ccc agg cag gcg tac gcc aac tac agg gac att gac ctc ggc agg       1392
```

```
                Asn Pro Arg Gln Ala Tyr Ala Asn Tyr Arg Asp Ile Asp Leu Gly Arg
                    450                 455                 460 aac gag gtg gtg aac gac atc tca acc tat agc agc ggc aag gtt tgg            1440
Asn Glu Val Val Asn Asp Ile Ser Thr Tyr Ser Ser Gly Lys Val Trp
465                 470                 475                 480 ggc gag aag tac ttc aag ggc aac ttc caa agg ctc gct att acc aag            1488
Gly Glu Lys Tyr Phe Lys Gly Asn Phe Gln Arg Leu Ala Ile Thr Lys
                485                 490                 495 ggc aag gtg gat cct cag gac tac ttc agg aac gag cag agc atc ccg            1536
Gly Lys Val Asp Pro Gln Asp Tyr Phe Arg Asn Glu Gln Ser Ile Pro
            500                 505                 510 ccg ctg ctc gag aag tac tga tcgaggacct tgcatggaga tttagtgcgt               1587
Pro Leu Leu Glu Lys Tyr
            515 ggttgccgtt tcacat                                                          1603

<210> SEQ ID NO 8
<211> LENGTH: 518
<212> TYPE: PRT
<213> ORGANISM: Triticum aestivum

<400> SEQUENCE: 8

Asn Tyr Arg Ala Phe Thr Leu Val Leu Leu Phe Cys Ala Leu Ser Cys
1               5                   10                  15

Gln Ala Ala Thr Tyr Ala Pro Val Pro Ala Lys Glu Asp Phe Leu
            20                  25                  30

Gly Cys Leu Met Lys Glu Ile Pro Ala Arg Leu Leu Tyr Ala Lys Ser
                35                  40                  45

Ser Pro Asp Phe Pro Thr Val Leu Ala Gln Thr Ile Arg Asn Ser Arg
        50                  55                  60

Trp Leu Ser Pro Gln Asn Val Lys Pro Leu Tyr Ile Ile Thr Pro Thr
65                  70                  75                  80

Asn Ala Ser His Ile Gln Ser Ala Val Val Cys Gly Arg Arg His Ser
                85                  90                  95

Val Arg Leu Arg Val Arg Ser Gly Gly His Asp Tyr Glu Gly Leu Ser
            100                 105                 110

Tyr Arg Ser Glu Lys Pro Glu Thr Phe Ala Val Val Asp Leu Asn Lys
        115                 120                 125

Met Arg Ala Val Leu Ile Asp Gly Tyr Ala Arg Thr Ala Trp Val Glu
130                 135                 140

Ser Gly Ala Gln Leu Gly Glu Leu Tyr Tyr Ala Ile Ala Lys Asn Ser
145                 150                 155                 160

Pro Val Leu Ala Phe Pro Ala Gly Val Cys Pro Thr Ile Gly Val Gly
                165                 170                 175

Gly Asn Phe Ala Gly Gly Gly Phe Gly Met Leu Leu Arg Lys Tyr Gly
            180                 185                 190

Ile Ala Ala Glu Asn Val Ile Asp Val Lys Val Asp Pro Asn Gly
        195                 200                 205

Lys Leu Leu Asp Lys Ser Ser Met Ser Pro Asp His Phe Trp Ala Val
210                 215                 220

Arg Gly Gly Gly Gly Glu Ser Phe Gly Ile Val Val Ser Trp Gln Val
225                 230                 235                 240

Lys Leu Leu Pro Val Pro Thr Val Thr Val Phe Lys Ile Pro Lys
                245                 250                 255

Thr Val Gln Glu Gly Ala Val Asp Leu Val Asn Lys Trp Gln Leu Val
            260                 265                 270
```

-continued

```
Gly Pro Ala Leu Pro Gly Asp Leu Met Ile Arg Val Ile Ala Ala Gly
            275                 280                 285

Asn Thr Ala Thr Phe Glu Gly Met Tyr Leu Gly Thr Cys Gln Thr Leu
290                 295                 300

Thr Pro Leu Met Ser Ser Gln Phe Pro Glu Leu Gly Met Asn Pro Tyr
305                 310                 315                 320

His Cys Asn Glu Met Pro Trp Ile Lys Ser Ile Pro Phe Ile His Leu
                325                 330                 335

Gly Lys Glu Ala Ser Leu Val Asp Leu Leu Asn Arg Asn Asn Thr Phe
            340                 345                 350

Lys Pro Phe Ala Glu Tyr Lys Ser Asp Tyr Val Tyr Gln Pro Phe Pro
        355                 360                 365

Lys Pro Val Trp Glu Gln Ile Phe Gly Trp Leu Thr Lys Pro Gly Gly
    370                 375                 380

Gly Met Met Ile Met Asp Pro Tyr Gly Ala Thr Ile Ser Ala Thr Pro
385                 390                 395                 400

Glu Ala Ala Thr Pro Phe Pro His Arg Gln Gly Val Leu Phe Asn Ile
                405                 410                 415

Gln Tyr Val Asn Tyr Trp Phe Ala Glu Ala Ala Ala Ala Pro Leu
            420                 425                 430

Gln Trp Ser Lys Asp Met Tyr Asn Phe Met Glu Pro Tyr Val Ser Lys
        435                 440                 445

Asn Pro Arg Gln Ala Tyr Ala Asn Tyr Arg Asp Ile Asp Leu Gly Arg
    450                 455                 460

Asn Glu Val Val Asn Asp Ile Ser Thr Tyr Ser Ser Gly Lys Val Trp
465                 470                 475                 480

Gly Glu Lys Tyr Phe Lys Gly Asn Phe Gln Arg Leu Ala Ile Thr Lys
                485                 490                 495

Gly Lys Val Asp Pro Gln Asp Tyr Phe Arg Asn Glu Gln Ser Ile Pro
            500                 505                 510

Pro Leu Leu Glu Lys Tyr
        515
```

```
<210> SEQ ID NO 9
<211> LENGTH: 1603
<212> TYPE: DNA
<213> ORGANISM: Triticum aestivum
<220> FEATURE:
<221> NAME/KEY: CDS
<222> LOCATION: (1)..(1557)

<400> SEQUENCE: 9 aac tgt agg gcc ttc gcg cag gtg ctc ctc ttc ttc gcc ttg tcc tgc      48
Asn Cys Arg Ala Phe Ala Gln Val Leu Leu Phe Phe Ala Leu Ser Cys
1               5                  10                  15 caa gcc gcc gcc acc tac gcg ccg gtg cct gcc aag gag gac ttc ctc      96
Gln Ala Ala Ala Thr Tyr Ala Pro Val Pro Ala Lys Glu Asp Phe Leu
            20                  25                  30 gga tgc ctc atg aag gag ata ccg gcc cgc ctc ctc tac gcc aag agc     144
Gly Cys Leu Met Lys Glu Ile Pro Ala Arg Leu Leu Tyr Ala Lys Ser
        35                  40                  45 tcg cct gac tac ccc acc gtg ctg gcg cag acc atc agg aac tcg cgg     192
Ser Pro Asp Tyr Pro Thr Val Leu Ala Gln Thr Ile Arg Asn Ser Arg
    50                  55                  60 tgg tcg acg cag cag aac gtg aag ccg ctg tac atc atc acc ccc acc     240
Trp Ser Thr Gln Gln Asn Val Lys Pro Leu Tyr Ile Ile Thr Pro Thr
65                  70                  75                  80 aac gcc tcc cac atc caa tcc gcg gtg gtg tgc ggc cgc cgg cac ggc     288
```

```
                Asn Ala Ser His Ile Gln Ser Ala Val Val Cys Gly Arg Arg His Gly
                                85                  90                  95 gtc cgc ctc cgc gtg cgg agc ggc ggc cac gac tac gag ggc ctg tcg              336
Val Arg Leu Arg Val Arg Ser Gly Gly His Asp Tyr Glu Gly Leu Ser
            100                 105                 110 tac cgg tcc gag aaa ccc gag acg ttc gcc gtc gtc gac ctc aac aag              384
Tyr Arg Ser Glu Lys Pro Glu Thr Phe Ala Val Val Asp Leu Asn Lys
            115                 120                 125 atg cgg gca gtg gtt gtc gac ggc tac gcc cgc acg gcg tgg gtc gaa              432
Met Arg Ala Val Val Val Asp Gly Tyr Ala Arg Thr Ala Trp Val Glu
130                 135                 140 tcc ggc gcg cag ctc ggc gag ctc tac tac gcc atc gcg aag aac agc              480
Ser Gly Ala Gln Leu Gly Glu Leu Tyr Tyr Ala Ile Ala Lys Asn Ser
145                 150                 155                 160 ccc gtg ctc gcg ttc ccg gcc ggc gtc tgc ccg tcc atc ggc gtc ggc              528
Pro Val Leu Ala Phe Pro Ala Gly Val Cys Pro Ser Ile Gly Val Gly
                165                 170                 175 ggc aac ttc gca ggc ggc ggc ttc ggc atg ctg ctg cgc aag tac ggc              576
Gly Asn Phe Ala Gly Gly Gly Phe Gly Met Leu Leu Arg Lys Tyr Gly
                180                 185                 190 atc gcc gcc gag aac gtc atc gac gtc aag gtg gtc gac ccc gac ggc              624
Ile Ala Ala Glu Asn Val Ile Asp Val Lys Val Val Asp Pro Asp Gly
                195                 200                 205 aag ctg ctc gac aag agc tcc atg agc gcg gac cac ttc tgg gcc gtc              672
Lys Leu Leu Asp Lys Ser Ser Met Ser Ala Asp His Phe Trp Ala Val
            210                 215                 220 agg ggc ggc ggc gga gag agc ttc ggc atc gtc gtc tcg tgg cag gtg              720
Arg Gly Gly Gly Gly Glu Ser Phe Gly Ile Val Val Ser Trp Gln Val
225                 230                 235                 240 aag ctc atg cca gtg cct ccc acc gtc acc gtg ttt aag atc ccc aag              768
Lys Leu Met Pro Val Pro Pro Thr Val Thr Val Phe Lys Ile Pro Lys
                245                 250                 255 acg gtg caa gaa ggc gcc gta gac ctc gtc aac aag tgg cag ctg gtc              816
Thr Val Gln Glu Gly Ala Val Asp Leu Val Asn Lys Trp Gln Leu Val
            260                 265                 270 ggg ccg gca ctt ccc ggc gac ctc atg atc cgc gtc atc gct gcc ggg              864
Gly Pro Ala Leu Pro Gly Asp Leu Met Ile Arg Val Ile Ala Ala Gly
            275                 280                 285 aac acg gcg acg ttc gag gcc ttg tac ctg ggc acc tgc aaa acc ctg              912
Asn Thr Ala Thr Phe Glu Ala Leu Tyr Leu Gly Thr Cys Lys Thr Leu
290                 295                 300 acg ccg ctg atg agc agc caa ttc ccc gag ctt ggc atg aac ccc tat              960
Thr Pro Leu Met Ser Ser Gln Phe Pro Glu Leu Gly Met Asn Pro Tyr
305                 310                 315                 320 cac tgc aac gag atg ccc tgg atc aag tcc gtc ccc ttc atc cac ctc             1008
His Cys Asn Glu Met Pro Trp Ile Lys Ser Val Pro Phe Ile His Leu
                325                 330                 335 ggc aaa cag gct ggc ctg gac gac ctc ctc aac cgg aac aac acc ttc             1056
Gly Lys Gln Ala Gly Leu Asp Asp Leu Leu Asn Arg Asn Asn Thr Phe
            340                 345                 350 aag ccc ttc gcc gaa tac aag tcg gac tac gtg tac cag ccc ttc ccc             1104
Lys Pro Phe Ala Glu Tyr Lys Ser Asp Tyr Val Tyr Gln Pro Phe Pro
            355                 360                 365 aag ccc gtg tgg gag cag atc ttc ggc tgg ctc gcg aag ccc ggc gcg             1152
Lys Pro Val Trp Glu Gln Ile Phe Gly Trp Leu Ala Lys Pro Gly Ala
            370                 375                 380 ggg atc atg atc atg gac ccc tac ggc gcc acc atc agc gcc acc ccc             1200
Gly Ile Met Ile Met Asp Pro Tyr Gly Ala Thr Ile Ser Ala Thr Pro
385                 390                 395                 400 gaa gcg gcg acg ccg ttc cct cac cgc cag ggc gtc ctc ttc aac atc             1248
```

```
                                                                                1296
cag tat gtc aac tac tgg ttc gcc gag cca gcc ggc gcc gcg ccg ctg
Gln Tyr Val Asn Tyr Trp Phe Ala Glu Pro Ala Gly Ala Ala Pro Leu
        420                 425                 430

1344
cag tgg agc aag gac att tac aat ttc atg gag ccg tac gtg agc aag
Gln Trp Ser Lys Asp Ile Tyr Asn Phe Met Glu Pro Tyr Val Ser Lys
            435                 440                 445

1392
aac ccc agg cag gcg tac gcc aac tac agg gac atc gac ctc ggc agg
Asn Pro Arg Gln Ala Tyr Ala Asn Tyr Arg Asp Ile Asp Leu Gly Arg
        450                 455                 460

1440
aat gag gtg gtg aac gac atc tca acc tac agc agc ggc aag gtg tgg
Asn Glu Val Val Asn Asp Ile Ser Thr Tyr Ser Ser Gly Lys Val Trp
465                 470                 475                 480

1488
ggc gag aag tac ttc aag agc aac ttc caa agg ctc gcc att acc aag
Gly Glu Lys Tyr Phe Lys Ser Asn Phe Gln Arg Leu Ala Ile Thr Lys
                485                 490                 495

1536
ggc aag gta gat cct cag gac tac ttc agg aat gag caa agc atc ccg
Gly Lys Val Asp Pro Gln Asp Tyr Phe Arg Asn Glu Gln Ser Ile Pro
            500                 505                 510

1587
ccg ctg atc gag aag tac tga tcgaggacct tgcatggaga tttagtgcgt
Pro Leu Ile Glu Lys Tyr
            515

1603
ggttggcgtt tcacat

<210> SEQ ID NO 10
<211> LENGTH: 518
<212> TYPE: PRT
<213> ORGANISM: Triticum aestivum

<400> SEQUENCE: 10

Asn Cys Arg Ala Phe Ala Gln Val Leu Leu Phe Phe Ala Leu Ser Cys
1               5                   10                  15

Gln Ala Ala Ala Thr Tyr Ala Pro Val Pro Ala Lys Glu Asp Phe Leu
            20                  25                  30

Gly Cys Leu Met Lys Glu Ile Pro Ala Arg Leu Leu Tyr Ala Lys Ser
        35                  40                  45

Ser Pro Asp Tyr Pro Thr Val Leu Ala Gln Thr Ile Arg Asn Ser Arg
    50                  55                  60

Trp Ser Thr Gln Gln Asn Val Lys Pro Leu Tyr Ile Ile Thr Pro Thr
65                  70                  75                  80

Asn Ala Ser His Ile Gln Ser Ala Val Val Cys Gly Arg Arg His Gly
                85                  90                  95

Val Arg Leu Arg Val Arg Ser Gly Gly His Asp Tyr Glu Gly Leu Ser
            100                 105                 110

Tyr Arg Ser Glu Lys Pro Glu Thr Phe Ala Val Val Asp Leu Asn Lys
        115                 120                 125

Met Arg Ala Val Val Asp Gly Tyr Ala Arg Thr Ala Trp Val Glu
    130                 135                 140

Ser Gly Ala Gln Leu Gly Glu Leu Tyr Tyr Ala Ile Ala Lys Asn Ser
145                 150                 155                 160

Pro Val Leu Ala Phe Pro Ala Gly Val Cys Pro Ser Ile Gly Val Gly
                165                 170                 175

Gly Asn Phe Ala Gly Gly Gly Phe Gly Met Leu Leu Arg Lys Tyr Gly
            180                 185                 190

Ile Ala Ala Glu Asn Val Ile Asp Val Lys Val Val Asp Pro Asp Gly
        195                 200                 205
```

```
Lys Leu Leu Asp Lys Ser Ser Met Ser Ala Asp His Phe Trp Ala Val
            210                 215                 220
Arg Gly Gly Gly Glu Ser Phe Gly Ile Val Val Ser Trp Gln Val
225                 230                 235                 240
Lys Leu Met Pro Val Pro Pro Thr Val Thr Val Phe Lys Ile Pro Lys
                    245                 250                 255
Thr Val Gln Glu Gly Ala Val Asp Leu Val Asn Lys Trp Gln Leu Val
                260                 265                 270
Gly Pro Ala Leu Pro Gly Asp Leu Met Ile Arg Val Ile Ala Ala Gly
            275                 280                 285
Asn Thr Ala Thr Phe Glu Ala Leu Tyr Leu Gly Thr Cys Lys Thr Leu
        290                 295                 300
Thr Pro Leu Met Ser Ser Gln Phe Pro Glu Leu Gly Met Asn Pro Tyr
305                 310                 315                 320
His Cys Asn Glu Met Pro Trp Ile Lys Ser Val Pro Phe Ile His Leu
                    325                 330                 335
Gly Lys Gln Ala Gly Leu Asp Asp Leu Leu Asn Arg Asn Asn Thr Phe
                340                 345                 350
Lys Pro Phe Ala Glu Tyr Lys Ser Asp Tyr Val Tyr Gln Pro Phe Pro
            355                 360                 365
Lys Pro Val Trp Glu Gln Ile Phe Gly Trp Leu Ala Lys Pro Gly Ala
        370                 375                 380
Gly Ile Met Ile Met Asp Pro Tyr Gly Ala Thr Ile Ser Ala Thr Pro
385                 390                 395                 400
Glu Ala Ala Thr Pro Phe Pro His Arg Gln Gly Val Leu Phe Asn Ile
                    405                 410                 415
Gln Tyr Val Asn Tyr Trp Phe Ala Glu Pro Ala Gly Ala Ala Pro Leu
                420                 425                 430
Gln Trp Ser Lys Asp Ile Tyr Asn Phe Met Glu Pro Tyr Val Ser Lys
            435                 440                 445
Asn Pro Arg Gln Ala Tyr Ala Asn Tyr Arg Asp Ile Asp Leu Gly Arg
        450                 455                 460
Asn Glu Val Val Asn Asp Ile Ser Thr Tyr Ser Ser Gly Lys Val Trp
465                 470                 475                 480
Gly Glu Lys Tyr Phe Lys Ser Asn Phe Gln Arg Leu Ala Ile Thr Lys
                    485                 490                 495
Gly Lys Val Asp Pro Gln Asp Tyr Phe Arg Asn Glu Gln Ser Ile Pro
                500                 505                 510
Pro Leu Ile Glu Lys Tyr
            515

<210> SEQ ID NO 11
<211> LENGTH: 1503
<212> TYPE: DNA
<213> ORGANISM: Phleum pratense
<220> FEATURE:
<221> NAME/KEY: CDS
<222> LOCATION: (1)..(1503)

<400> SEQUENCE: 11 tac ttc ccg ccg ccg gct gct aaa gaa gac ttc ctg ggt tgc ctg gtt     48
Tyr Phe Pro Pro Pro Ala Ala Lys Glu Asp Phe Leu Gly Cys Leu Val
1               5                   10                  15 aaa gaa atc ccg ccg cgt ctg ttg tac gcg aaa tcg tcg ccg gcg tat     96
Lys Glu Ile Pro Pro Arg Leu Leu Tyr Ala Lys Ser Ser Pro Ala Tyr
            20                  25                  30 ccc tca gtc ctg ggg cag acc atc cgg aac tcg agg tgg tcg tcg ccg    144
```

-continued

```
      Pro Ser Val Leu Gly Gln Thr Ile Arg Asn Ser Arg Trp Ser Ser Pro
                   35                  40                  45 gac aac gtg aag ccg ctc tac atc atc acc ccc acc aac gtc tcc cac      192
Asp Asn Val Lys Pro Leu Tyr Ile Ile Thr Pro Thr Asn Val Ser His
 50                  55                  60 atc cag tcc gcc gtg gtg tgc ggc cgc cgc cac agc gtc cgc atc cgc      240
Ile Gln Ser Ala Val Val Cys Gly Arg Arg His Ser Val Arg Ile Arg
 65                  70                  75                  80 gtg cgc agc ggc ggg cac gac tac gag ggc ctc tcg tac cgg tct ttg      288
Val Arg Ser Gly Gly His Asp Tyr Glu Gly Leu Ser Tyr Arg Ser Leu
                 85                  90                  95 cag ccc gag acg ttc gcc gtc gtc gac ctc aac aag atg cgg gcg gtg      336
Gln Pro Glu Thr Phe Ala Val Val Asp Leu Asn Lys Met Arg Ala Val
            100                 105                 110 tgg gtg gac ggc aag gcc cgc acg gcg tgg gtg gac tcc ggc gcg cag      384
Trp Val Asp Gly Lys Ala Arg Thr Ala Trp Val Asp Ser Gly Ala Gln
            115                 120                 125 ctc ggc gag ctc tac tac gcc atc tat aag gcg agc ccc acg ctg gcg      432
Leu Gly Glu Leu Tyr Tyr Ala Ile Tyr Lys Ala Ser Pro Thr Leu Ala
130                 135                 140 ttc ccg gcc ggc gtg tgc ccg acg atc gga gtg ggc ggc aac ttc gcg      480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcc gcg gag      528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc aag ctg cac gac      576
Asn Val Ile Asp Val Lys Leu Val Asp Ala Asn Gly Lys Leu His Asp
            180                 185                 190 aag aag tcc atg ggc gac gac cat ttc tgg gcc gtc agg ggc ggc ggg      624
Lys Lys Ser Met Gly Asp Asp His Phe Trp Ala Val Arg Gly Gly Gly
            195                 200                 205 ggc gag agc ttc ggc atc gtg gtc gcg tgg cag gtg aag ctc ctg ccg      672
Gly Glu Ser Phe Gly Ile Val Val Ala Trp Gln Val Lys Leu Leu Pro
210                 215                 220 gtg ccg ccc acc gtg aca ata ttc aag atc tcc aag aca gtg agc gag      720
Val Pro Pro Thr Val Thr Ile Phe Lys Ile Ser Lys Thr Val Ser Glu
225                 230                 235                 240 ggc gcc gtg gac atc atc aac aag tgg caa gtg gtc gcg ccg cag ctt      768
Gly Ala Val Asp Ile Ile Asn Lys Trp Gln Val Val Ala Pro Gln Leu
                245                 250                 255 ccc gcc gac ctc atg atc cgc atc atc gcg cag ggg ccc aag gcc acg      816
Pro Ala Asp Leu Met Ile Arg Ile Ile Ala Gln Gly Pro Lys Ala Thr
            260                 265                 270 ttc gag gcc atg tac ctc ggc acc tgc aaa acc ctg acg ccg ttg atg      864
Phe Glu Ala Met Tyr Leu Gly Thr Cys Lys Thr Leu Thr Pro Leu Met
            275                 280                 285 agc agc aag ttc ccg gag ctc ggc atg aac ccc tcc cac tgc aac gag      912
Ser Ser Lys Phe Pro Glu Leu Gly Met Asn Pro Ser His Cys Asn Glu
            290                 295                 300 atg tca tgg atc cag tcc atc ccc ttc gtc cac ctc ggc cac agg gac      960
Met Ser Trp Ile Gln Ser Ile Pro Phe Val His Leu Gly His Arg Asp
305                 310                 315                 320 gcc ctc gag gac gac ctc ctc aac cgg aac aac tcc ttc aag ccc ttc     1008
Ala Leu Glu Asp Asp Leu Leu Asn Arg Asn Asn Ser Phe Lys Pro Phe
                325                 330                 335 gcc gaa tac aag tcc gac tac gtc tac cag ccc ttc ccc aag acc gtc     1056
Ala Glu Tyr Lys Ser Asp Tyr Val Tyr Gln Pro Phe Pro Lys Thr Val
            340                 345                 350 tgg gag cag atc ctc aac acc tgg ctc gtc aag ccc ggc gcc ggg atc     1104
```

-continued

```
Trp Glu Gln Ile Leu Asn Thr Trp Leu Val Lys Pro Gly Ala Gly Ile
            355                 360                 365 atg atc ttc gac ccc tac ggc gcc acc atc agc gcc acc ccg gag tcc      1152
Met Ile Phe Asp Pro Tyr Gly Ala Thr Ile Ser Ala Thr Pro Glu Ser
    370                 375                 380 gcc acg ccc ttc cct cac cgc aag ggc gtc ctc ttc aac atc cag tac      1200
Ala Thr Pro Phe Pro His Arg Lys Gly Val Leu Phe Asn Ile Gln Tyr
385                 390                 395                 400 gtc aac tac tgg ttc gcc ccg gga gcc gcc gcg ccc ctc tcg tgg          1248
Val Asn Tyr Trp Phe Ala Pro Gly Ala Ala Ala Pro Leu Ser Trp
                405                 410                 415 agc aag gac atc tac aac tac atg gag ccc tac gtg agc aag aac ccc      1296
Ser Lys Asp Ile Tyr Asn Tyr Met Glu Pro Tyr Val Ser Lys Asn Pro
            420                 425                 430 agg cag gcg tac gca aac tac agg gac atc gac ctc ggc agg aac gag      1344
Arg Gln Ala Tyr Ala Asn Tyr Arg Asp Ile Asp Leu Gly Arg Asn Glu
        435                 440                 445 gtg gtc aac gac gtc tcc acc tac gcc agc ggc aag gtc tgg ggc cag      1392
Val Val Asn Asp Val Ser Thr Tyr Ala Ser Gly Lys Val Trp Gly Gln
450                 455                 460 aaa tac ttc aag ggc aac ttc gag agg ctc gcc att acc aag ggc aag      1440
Lys Tyr Phe Lys Gly Asn Phe Glu Arg Leu Ala Ile Thr Lys Gly Lys
465                 470                 475                 480 gtc gat cct acc gac tac ttc agg aac gag cag agc atc ccg ccg ctc      1488
Val Asp Pro Thr Asp Tyr Phe Arg Asn Glu Gln Ser Ile Pro Pro Leu
                485                 490                 495 atc aaa aag tac tga                                                  1503
Ile Lys Lys Tyr
            500

<210> SEQ ID NO 12
<211> LENGTH: 500
<212> TYPE: PRT
<213> ORGANISM: Phleum pratense

<400> SEQUENCE: 12

Tyr Phe Pro Pro Ala Ala Lys Glu Asp Phe Leu Gly Cys Leu Val
1               5                   10                  15

Lys Glu Ile Pro Pro Arg Leu Leu Tyr Ala Lys Ser Ser Pro Ala Tyr
            20                  25                  30

Pro Ser Val Leu Gly Gln Thr Ile Arg Asn Ser Arg Trp Ser Ser Pro
        35                  40                  45

Asp Asn Val Lys Pro Leu Tyr Ile Ile Thr Pro Thr Asn Val Ser His
    50                  55                  60

Ile Gln Ser Ala Val Val Cys Gly Arg His Ser Val Arg Ile Arg
65                  70                  75                  80

Val Arg Ser Gly Gly His Asp Tyr Glu Gly Leu Ser Tyr Arg Ser Leu
                85                  90                  95

Gln Pro Glu Thr Phe Ala Val Val Asp Leu Asn Lys Met Arg Ala Val
            100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile Tyr Lys Ala Ser Pro Thr Leu Ala
    130                 135                 140

Phe Pro Ala Gly Val Cys Pro Thr Ile Gly Val Gly Asn Phe Ala
145                 150                 155                 160

Gly Gly Gly Phe Gly Met Leu Leu Arg Lys Tyr Gly Ile Ala Ala Glu
                165                 170                 175
```

-continued

```
Asn Val Ile Asp Val Lys Leu Val Asp Ala Asn Gly Lys Leu His Asp
            180                 185                 190
Lys Lys Ser Met Gly Asp Asp His Phe Trp Ala Val Arg Gly Gly Gly
        195                 200                 205
Gly Glu Ser Phe Gly Ile Val Val Ala Trp Gln Val Lys Leu Leu Pro
    210                 215                 220
Val Pro Pro Thr Val Thr Ile Phe Lys Ile Ser Lys Thr Val Ser Glu
225                 230                 235                 240
Gly Ala Val Asp Ile Ile Asn Lys Trp Gln Val Val Ala Pro Gln Leu
                245                 250                 255
Pro Ala Asp Leu Met Ile Arg Ile Ile Ala Gln Gly Pro Lys Ala Thr
            260                 265                 270
Phe Glu Ala Met Tyr Leu Gly Thr Cys Lys Thr Leu Thr Pro Leu Met
        275                 280                 285
Ser Ser Lys Phe Pro Glu Leu Gly Met Asn Pro Ser His Cys Asn Glu
    290                 295                 300
Met Ser Trp Ile Gln Ser Ile Pro Phe Val His Leu Gly His Arg Asp
305                 310                 315                 320
Ala Leu Glu Asp Asp Leu Leu Asn Arg Asn Asn Ser Phe Lys Pro Phe
                325                 330                 335
Ala Glu Tyr Lys Ser Asp Tyr Val Tyr Gln Pro Phe Pro Lys Thr Val
            340                 345                 350
Trp Glu Gln Ile Leu Asn Thr Trp Leu Val Lys Pro Gly Ala Gly Ile
        355                 360                 365
Met Ile Phe Asp Pro Tyr Gly Ala Thr Ile Ser Ala Thr Pro Glu Ser
    370                 375                 380
Ala Thr Pro Phe Pro His Arg Lys Gly Val Leu Phe Asn Ile Gln Tyr
385                 390                 395                 400
Val Asn Tyr Trp Phe Ala Pro Gly Ala Ala Ala Pro Leu Ser Trp
                405                 410                 415
Ser Lys Asp Ile Tyr Asn Tyr Met Glu Pro Tyr Val Ser Lys Asn Pro
            420                 425                 430
Arg Gln Ala Tyr Ala Asn Tyr Arg Asp Ile Asp Leu Gly Arg Asn Glu
        435                 440                 445
Val Val Asn Asp Val Ser Thr Tyr Ala Ser Gly Lys Val Trp Gly Gln
    450                 455                 460
Lys Tyr Phe Lys Gly Asn Phe Glu Arg Leu Ala Ile Thr Lys Gly Lys
465                 470                 475                 480
Val Asp Pro Thr Asp Tyr Phe Arg Asn Glu Gln Ser Ile Pro Pro Leu
                485                 490                 495
Ile Lys Lys Tyr
        500

<210> SEQ ID NO 13
<211> LENGTH: 12
<212> TYPE: PRT
<213> ORGANISM: Dactylus glomerata

<400> SEQUENCE: 13

Asp Ile Tyr Asn Tyr Met Glu Pro Tyr Val Ser Lys
1               5                   10

<210> SEQ ID NO 14
<211> LENGTH: 11
<212> TYPE: PRT
<213> ORGANISM: Dactylus glomerata
```

```
<400> SEQUENCE: 14

Val Asp Pro Thr Asp Tyr Phe Gly Asn Glu Gln
1               5                   10

<210> SEQ ID NO 15
<211> LENGTH: 17
<212> TYPE: PRT
<213> ORGANISM: Dactylus glomerata

<400> SEQUENCE: 15

Ala Arg Thr Ala Trp Val Asp Ser Gly Ala Gln Leu Gly Glu Leu Ser
1               5                   10                  15

Tyr

<210> SEQ ID NO 16
<211> LENGTH: 15
<212> TYPE: PRT
<213> ORGANISM: Dactylus glomerata

<400> SEQUENCE: 16

Gly Val Leu Phe Asn Ile Gln Tyr Val Asn Tyr Trp Phe Ala Pro
1               5                   10                  15

<210> SEQ ID NO 17
<211> LENGTH: 11
<212> TYPE: PRT
<213> ORGANISM: Cynodon dactylon

<400> SEQUENCE: 17

Lys Thr Val Lys Pro Leu Tyr Ile Ile Thr Pro
1               5                   10

<210> SEQ ID NO 18
<211> LENGTH: 22
<212> TYPE: PRT
<213> ORGANISM: Cynodon dactylon

<400> SEQUENCE: 18

Lys Gln Val Glu Arg Asp Phe Leu Thr Ser Leu Thr Lys Asp Ile Pro
1               5                   10                  15

Gln Leu Tyr Leu Lys Ser
            20

<210> SEQ ID NO 19
<211> LENGTH: 16
<212> TYPE: PRT
<213> ORGANISM: Cynodon dactylon

<400> SEQUENCE: 19

Thr Val Lys Pro Leu Tyr Ile Ile Thr Pro Ile Thr Ala Ala Met Ile
1               5                   10                  15

<210> SEQ ID NO 20
<211> LENGTH: 24
<212> TYPE: PRT
<213> ORGANISM: Cynodon dactylon

<400> SEQUENCE: 20

Leu Arg Lys Tyr Gly Thr Ala Ala Asp Asn Val Ile Asp Ala Lys Val
1               5                   10                  15

Val Asp Ala Gln Gly Arg Leu Leu
            20
```

```
<210> SEQ ID NO 21
<211> LENGTH: 14
<212> TYPE: PRT
<213> ORGANISM: Cynodon dactylon

<400> SEQUENCE: 21

Lys Trp Gln Thr Val Ala Pro Ala Leu Pro Asp Pro Asn Met
1               5                   10

<210> SEQ ID NO 22
<211> LENGTH: 15
<212> TYPE: PRT
<213> ORGANISM: Cynodon dactylon

<400> SEQUENCE: 22

Val Thr Trp Ile Glu Ser Val Pro Tyr Ile Pro Met Gly Asp Lys
1               5                   10                  15

<210> SEQ ID NO 23
<211> LENGTH: 19
<212> TYPE: PRT
<213> ORGANISM: Cynodon dactylon
<220> FEATURE:
<221> NAME/KEY: MOD_RES
<222> LOCATION: (8)
<223> OTHER INFORMATION: variable amino acid

<400> SEQUENCE: 23

Gly Thr Val Arg Asp Leu Leu Xaa Arg Thr Ser Asn Ile Lys Ala Phe
1               5                   10                  15

Gly Lys Tyr

<210> SEQ ID NO 24
<211> LENGTH: 23
<212> TYPE: PRT
<213> ORGANISM: Cynodon dactylon

<400> SEQUENCE: 24

Thr Ser Asn Ile Lys Ala Phe Gly Lys Tyr Lys Ser Asp Tyr Val Leu
1               5                   10                  15

Glu Pro Ile Pro Lys Lys Ser
            20

<210> SEQ ID NO 25
<211> LENGTH: 13
<212> TYPE: PRT
<213> ORGANISM: Cynodon dactylon

<400> SEQUENCE: 25

Tyr Arg Asp Leu Asp Leu Gly Val Asn Gln Val Val Gly
1               5                   10

<210> SEQ ID NO 26
<211> LENGTH: 15
<212> TYPE: PRT
<213> ORGANISM: Cynodon dactylon

<400> SEQUENCE: 26

Ser Ala Thr Pro Pro Thr His Arg Ser Gly Val Leu Phe Asn Ile
1               5                   10                  15

<210> SEQ ID NO 27
<211> LENGTH: 36
<212> TYPE: PRT
<213> ORGANISM: Cynodon dactylon
```

-continued

<400> SEQUENCE: 27

Ala Ala Ala Ala Leu Pro Thr Gln Val Thr Arg Asp Ile Tyr Ala Phe
1               5                   10                  15

Met Thr Pro Tyr Val Ser Lys Asn Pro Arg Gln Ala Tyr Val Asn Tyr
            20                  25                  30

Arg Asp Leu Asp
        35

<210> SEQ ID NO 28
<211> LENGTH: 14
<212> TYPE: PRT
<213> ORGANISM: Lolium perenne

<400> SEQUENCE: 28

Phe Leu Glu Pro Val Leu Gly Leu Ile Phe Pro Ala Gly Val
1               5                   10

<210> SEQ ID NO 29
<211> LENGTH: 9
<212> TYPE: PRT
<213> ORGANISM: Lolium perenne

<400> SEQUENCE: 29

Gly Leu Ile Glu Phe Pro Ala Gly Val
1               5

<210> SEQ ID NO 30
<211> LENGTH: 22
<212> TYPE: DNA
<213> ORGANISM: Secale cereale

<400> SEQUENCE: 30
ggctcccggg gcgaaccagt ag                                         22

<210> SEQ ID NO 31
<211> LENGTH: 23
<212> TYPE: DNA
<213> ORGANISM: Secale cereale

<400> SEQUENCE: 31
accaacgcct cccacatcca gtc                                        23

<210> SEQ ID NO 32
<211> LENGTH: 49
<212> TYPE: DNA
<213> ORGANISM: Secale cereale

<400> SEQUENCE: 32
gataagcttc tcgagtgatt agtactttt gatcagcggc gggatgctc              49

<210> SEQ ID NO 33
<211> LENGTH: 23
<212> TYPE: DNA
<213> ORGANISM: Secale cereale

<400> SEQUENCE: 33
gctctcgatc ggctacaatg gcg                                        23

<210> SEQ ID NO 34
<211> LENGTH: 25
<212> TYPE: DNA
<213> ORGANISM: Secale cereale

<400> SEQUENCE: 34

```
cacgcactac aaatctccat gcaag                                    25

<210> SEQ ID NO 35
<211> LENGTH: 30
<212> TYPE: DNA
<213> ORGANISM: Secale cereale

<400> SEQUENCE: 35
catgcttgat ccttattcta ctagttgggc                               30

<210> SEQ ID NO 36
<211> LENGTH: 30
<212> TYPE: DNA
<213> ORGANISM: Secale cereale

<400> SEQUENCE: 36
tacgcacgat ccttattcta ctagttgggc                               30

<210> SEQ ID NO 37
<211> LENGTH: 30
<212> TYPE: DNA
<213> ORGANISM: Hordeum vulgare

<400> SEQUENCE: 37
gccttgtcct gccaccacgc cgccgccacc                               30

<210> SEQ ID NO 38
<211> LENGTH: 23
<212> TYPE: DNA
<213> ORGANISM: Hordeum vulgare

<400> SEQUENCE: 38
gctctcgatc ggctacaatg gcg                                      23

<210> SEQ ID NO 39
<211> LENGTH: 25
<212> TYPE: DNA
<213> ORGANISM: Hordeum vulgare

<400> SEQUENCE: 39
cacgcactac aaatctccat gcaag                                    25

<210> SEQ ID NO 40
<211> LENGTH: 30
<212> TYPE: DNA
<213> ORGANISM: Hordeum vulgare

<400> SEQUENCE: 40
catgcttgat ccttattcta ctagttgggc                               30

<210> SEQ ID NO 41
<211> LENGTH: 23
<212> TYPE: DNA
<213> ORGANISM: Triticum aestivum

<400> SEQUENCE: 41
cacgcactaa atctccatgc aag                                      23

<210> SEQ ID NO 42
<211> LENGTH: 30
<212> TYPE: DNA
<213> ORGANISM: Triticum aestivum

<400> SEQUENCE: 42
```

```
tacgcacgat ccttattcta ctagttgggc                                    30

<210> SEQ ID NO 43
<211> LENGTH: 23
<212> TYPE: DNA
<213> ORGANISM: Triticum aestivum

<400> SEQUENCE: 43
aagctctatc gcctacaatg gcg                                           23

<210> SEQ ID NO 44
<211> LENGTH: 25
<212> TYPE: DNA
<213> ORGANISM: Triticum aestivum

<400> SEQUENCE: 44
ggtgctcctc ttctgcgcct tgtcc                                         25
```

DNA SEQUENCE, AND RECOMBINANT PREPARATION OF GROUP 4 MAJOR ALLERGENS FROM CEREALS

BACKGROUND OF THE INVENTION

The present invention relates to the provision of DNA sequences of group 4 major allergens from cereals (*Triticeae*). The invention also encompasses fragments, new combinations of partial sequences and point mutants having a hypoallergenic action. The recombinant DNA molecules and the derived polypeptides, fragments, new combinations of partial sequences and variants can be utilised for the therapy of pollen-allergic diseases. The proteins prepared by recombinant methods can be employed for in vitro and in vivo diagnosis of pollen allergies.

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are released by sources of various origin, such as plant pollen, mites, cats or dogs. Up to 40% of these type 1 allergy sufferers in turn exhibit specific IgE reactivity with grass pollen allergens, inter alia cereal pollen allergens (Freidhoff et al., 1986, J. Allergy Clin. Immunol. 78, 1190-2001). Of the cereal pollen allergens, the allergens of rye have particular importance.

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens, depending on the relative frequency with which the individual allergen molecules react with the IgE antibodies of allergy sufferers.

The allergens from the pollen of various species from the family of the grasses (*Poaceae*) are divided into groups which are homologous amongst one another.

In particular, the molecules of major allergen group 4 have high immunological cross-reactivity with one another both with monoclonal murine antibodies and also with human IgE antibodies (Fahlbusch et al., 1993 Clin. Exp. Allergy 23:51-60; Leduc-Brodard et al., 1996, J. Allergy Clin. Immunol. 98:1065-1072; Su et al., 1996, J. Allergy Clin. Immunol. 97:210; Fahlbusch et al., 1998, Clin. Exp. Allergy 28:799-807; Gavrovic-Jankulovic et al., 2000, Invest. Allergol. Clin. Immunol. 10 (6):361-367; Stumvoll et al. 2002, Biol. Chem. 383:1383-1396; Grote et al., 2002. Biol. Chem. 383:1441-1445; Andersson and Lidholm, 2003, Int. Arch. Allergy Immunol. 130:87-107; Mari, 2003, Clin. Exp. Allergy, 33 (1):43-51).

A complete DNA sequence is hitherto not known for any of the group 4 major allergens.

From the group 4 allergen from *Dactylus glomerata*, it has hitherto only been possible for peptides to be obtained by enzymatic degradation and sequenced:

| | |
|---|---|
| DIYNYMEPYVSK, | (SEQ ID NO 13) |
| VDPTDYFGNEQ, | (SEQ ID NO 14) |
| ARTAWVDSGAQLGELSY | (SEQ ID NO 15) |
| and | |
| GVLFNIQYVNYWFAP. | (SEQ ID NO 16, Leduc-Brodard et at., 1996, J. Allergy Clin. Immunol. 98: 1065-1072) |

Peptides have also been obtained from the group 4 allergen of sub-tropical Bermuda grass (*Cynodon dactylon*) by proteolysis and sequenced:

| | |
|---|---|
| KTVKPLYIITP, | (SEQ ID NO 17) |
| KQVERDFLTSLTKDIPQLYLKS, | (SEQ ID NO 18) |
| TVKPLYIITPITAAMI, | (SEQ ID NO 19) |
| LRKYGTAADNVIDAKWDAQGRLL, | (SEQ ID NO 20) |
| KWQTVAPALPDPNM, | (SEQ ID NO 21) |
| VTWIESVPYIPMGDK, | (SEQ ID NO 22) |
| GTVRDLLXRTSNIKAFGKY, | (SEQ ID NO 23) |
| TSNIKAFGKYKSDYVLEPIPKKS, | (SEQ ID NO 24) |
| YRDLDLGVNQWG, | (SEQ ID NO 25) |
| SATPPTHRSGVLFNI and | (SEQ ID NO 26) |
| AAAALPTQVTRDIYAFMTPYVSKNPRQ AYVNYRDLD, | (SEQ ID NO 27 Liaw et al., 2001, Biochem. Biophys. Research Communication 280: 738-743). |

For *Lolium perenne*, peptide fragments having the following sequences have been described for the basic group 4 allergen: FLEPVLGLIFPAGV (SEQ ID NO 28) and GLIEFPAGV (SEQ ID NO 29, Jaggi et al., 1989, Int. Arch. Allergy Appl. Immunol. 89: 342-348).

As the first sequence of a group 4 allergen, the still unpublished sequence of Phl p 4 from *Phleum pratense* (SEQ ID NO 11) has been elucidated by the inventors of the present patent application and described in International Application WO 04/000881.

Nothing is hitherto known on the sequences of the group 4 major allergens from cereals (*Triceae*).

The object on which the present invention was based therefore consisted in the provision of DNA sequences of group 4 major allergens from cereals, in particular the allergen Sec c 4 from rye (*Secale cerale*) (SEQ ID NO 1, 3), Hor v 4 from barley (*Hordeum vulgare*) (SEQ ID NO 5) and Tri a 4 from wheat (*Triticum aestivum*) (SEQ ID NO 7, 9) and of corresponding recombinant DNA molecules on the basis of which the allergens can be expressed as protein and made available, as such or in modified form, for pharmacologically significant exploitation. The sequence of Phl p 4 (SEQ ID NO 11) was the starting point for the present invention.

LIST OF SEQUENCES ACCORDING TO THE INVENTION

The DNA and protein sequences of the mature allergens in accordance with SEQ ID NO 1-10 are preceded by a signal sequence. The encoding region ends with the TGA or TAG stop codons in the DNA sequences.

DNA sequence of Sec c 4. (a) Isoform Sec c 4.01 (SEQ ID NO 1), (b) isoform Sec c 4.02 (SEQ ID NO 3).
Protein sequences (SEQ ID NO 2, 4) derived from DNA sequences in accordance with SEQ ID NO 1 and 3.
DNA sequence of Hor v 4 (SEQ ID NO 5).
Protein sequence (SEQ ID NO 6) derived from the DNA sequence in accordance with SEQ ID NO 5.
DNA sequence of Tri a 4. (a) Isoform Tri a 4.01 (SEQ ID NO 7), (b) isoform Tri a 4.02 (SEQ ID NO 9).
Protein sequences (SEQ ID NO 8, 10) derived from the DNA sequences in accordance with SEQ ID NO 7 and 9.
DNA sequence of Phl p 4 (SEQ ID NO 11), in accordance with SEQ ID NO 5 from WO 04/000881.
Protein sequence of Phl p 4 (SEQ ID NO 12), in accordance with SEQ ID NO 6 from WO 04/000881.

DESCRIPTION OF THE INVENTION

The present invention now provides for the first time DNA sequences of the cereal pollen major allergens Sec c 4, Hor v 4 and Tri a 4, in accordance with SEQ ID NO 1, 3, 5, 7, and 9.

The present invention therefore relates to DNA molecules selected from the nucleotide sequences in accordance with SEQ ID NO 1, 3, 5, 7, and 9.

The invention furthermore relates to sequences homologous to the DNA sequences according to the invention and corresponding DNA molecules of group 4 allergens from other *Poaceae*, such as, for example, *Lolium perenne, Dactylis glomerata, Poa pratensis, Cynodon dactylon* and *Holcus lanatus*, which, owing to the sequence homology that exists, hybridise with the DNA sequences according to the invention under stringent conditions, or have immunological cross-reactivity with respect to the allergens according to the invention.

The invention also encompasses fragments, new combinations of partial sequences and point mutants having a hypoallergenic action.

The invention therefore furthermore relates to corresponding partial sequences, a combination of partial sequences, or replacement, elimination or addition mutants which encode an immunomodulatory, T-cell-reactive fragment of a group 4 allergen from the *Poaceae*.

With knowledge of the DNA sequence of the naturally occurring allergens, it is now possible to prepare these allergens as recombinant proteins which can be used in the diagnosis and therapy of allergic diseases (Scheiner and Kraft, 1995, Allergy 50: 384-391).

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102 (4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed TH cell equilibrium in allergy sufferers is immunotherapeutic DNA vaccination, which involves treatment with expressible DNA which encodes the relevant allergens. Initial experimental evidence of allergen-specific influencing of the immune response has been furnished in rodents by injection of allergen-encoding DNA (Hsu et al., 1996, Nature Medicine 2 (5): 540-544).

The present invention therefore also relates to a DNA molecule described above or below as medicament and to a corresponding recombinant expression vector as medicament.

The corresponding proteins prepared by recombinant methods can be employed for therapy and for in vitro and in vivo diagnosis of pollen allergies.

For preparation of the recombinant allergen, the cloned nucleic acid is ligated into an expression vector, and this construct is expressed in a suitable host organism. After biochemical purification, this recombinant allergen is available for detection of IgE antibodies by established methods.

The present invention therefore furthermore relates to a recombinant expression vector comprising a DNA molecule described above or below, functionally linked to an expression control sequence, and a host organism transformed with said DNA molecule or said expression vector.

The invention also relates to the use of at least one DNA molecule described above or at least one expression vector described above for the preparation of a medicament for the immunotherapeutic DNA vaccination of patients with allergies in the triggering of which group 4 allergens from the *Poaceae*, preferably *Triticeae*, in particular Sec c 4, Hor v 4, Tri a 4, are involved and/or for the prevention of such allergies.

As already stated, the invention can be used as an essential component in a recombinant allergen- or nucleic acid-containing preparation for specific immunotherapy. A number of possibilities arise here. On the one hand, the protein with an unchanged primary structure may be a constituent of the preparation. On the other hand, a hypoallergenic (allergoid) form can be used in accordance with the invention for therapy in order to avoid undesired side effects by specific deletion of IgE epitopes of the molecule as a whole or the production of individual fragments which encode T-cell epitopes. Finally, the nucleic acid per se, if ligated with a eukaryotic expression vector, gives a preparation which, when applied directly, modifies the allergic immune state in the therapeutic sense.

The present invention furthermore relates to the polypeptides encoded by one or more of the DNA molecules described above, preferably in their property as medicament.

These are proteins corresponding to an amino acid sequence in accordance with SEQ ID NO 2, 4, 6, 8 or 10. In particular, these are mature proteins (without signal sequence component), beginning with amino acid 23 (SEQ ID NO 2, 4 and 6) and with amino acid 22 (SEQ ID NO 8, 10). The invention furthermore relates to proteins which contain these amino acid sequences or parts of these sequences.

The invention accordingly also relates to a process for the preparation of such polypeptides by cultivation of a host organism and isolation of the corresponding polypeptide from the culture.

The invention likewise relates to the use of at least one polypeptide described above for the preparation of a medicament for the diagnosis and/or treatment of allergies in the triggering of which group 4 allergens from the *Poaceae*, preferably *Triticeae*, in particular Sec c 4, Hor v 4, Tri a 4, are involved and for the prevention of such allergies.

When determining the protein and DNA sequences according to the invention, the following procedure was followed:

Sec c 4 From Rye

1. Starting from the DNA sequence of Phl p 4 (SEQ ID NO 12, WO 04/000881), specific primers (Table 1) derived from the Phl p 4 sequence were generated. Five clones were obtained from rye pollen DNA by PCR with primers #87 and #83. The amplified Sec c 4 gene fragment 1 corresponding to these clones encodes a polypeptide corresponding to amino acids 68-401 of Phl p 4 (SEQ ID NO 12).

2. An EST database search was carried out with the partial Sec c 4 sequence. However, no homologous sequences were found in EST data-bases specialising in rye. Instead, individual, homologous, non-overlapping EST fragments were found in EST databases specialising in barley and wheat. Individual EST fragments extend into the 5'-UTR region and others into the 3'-UTR region (UTR=untranslated region) of the corresponding genes.

3. However, a complete group 4 gene from wheat or barley cannot be constructed from the EST sequences found in the databases since these sequences do not overlap and a homologous group 4 gene is not known. However, it was possible to assign these EST sequences with reference to the Phl p 4 sequence (SEQ ID NO 11) and the Sec c 4 fragment obtained in step 1 and these served as template for the preparation of PCR primers.

4. With the aid of primers #195 and #189 prepared in this way, three clones were obtained by PCR. Primer #195 was derived from a barley EST sequence, primer #189 is a Phl p 4-specific primer and overlaps the Phl p 4 stop codon and the codons of the 10 C-terminal Phl p 4 amino acids. The Sec c 4 gene fragment 2 amplified in this way encodes a polypeptide, beginning within the signal sequence and ending with the position corresponding to position 490 of Phl p 4. This polypeptide covers the N terminal of Sec c 4.

5a. Three further clones were obtained by PCR with primers #195 and #202. Both primers were derived from barley EST sequences. The amplified Sec c 4 gene 3 encodes the corresponding amino acids beginning within the signal sequence and ending at the C terminal of Sec c 4. The complete sequence of mature Sec c 4 is thus present in the sequence determined.

The next two steps 5b and 5c serve to double-check the result obtained in step 5a:

5b. A further clone was obtained by PCR with primers #195 and #203. Primer #195 was derived from a barley EST sequence, primer #203 from a wheat EST sequence. The amplified Sec c 4 gene encodes the corresponding amino acids beginning within the signal sequence and ending at the C terminal of Sec c 4. The complete sequence of mature Sec c 4 is therefore present in the sequence determined.

5c. A further clone was obtained by PCR with primers #195 and #198. Also primer #198 The amplified Sec c 4 gene encodes the corresponding amino acids beginning within the signal sequence and ending at the C terminal of Sec c 4. The complete sequence of mature Sec c 4 is therefore present in the sequence determined.

Two isoforms Sec c 4.01 and 4.02 were found. The mature allergens begin with amino acid 23 of the sequences in accordance with SEQ ID NO 2, 4 and 6.

Hor v 4 From Barley

With the aid of the Sec c 4 sequences obtained as described above, homologous EST fragments were found in EST databases of *Hordeum vulgare*. These fragments overlap, but not to give a complete gene. With reference to the EST sequences found, however, it was possible to generate Hor v 4-specific primers, which were used for amplification of the Hor v 4 gene from genomic DNA.

In total, 15 clones were analysed.

4 clones were obtained by PCR with primers #195 and #198.

4 clones were obtained by PCR with primers #195 and #202.

3 clones were obtained by PCR with primers #194 and #198.

4 clones were obtained by PCR with primers #194 and #202.

The derived protein sequence begins within the signal sequence of Hor v 4 and extends to the C-terminal end of the protein (from amino acid 23 of SEQ ID NO 6).

Tri a 4 From Wheat

With the aid of the Sec c 4 sequences obtained as described above, homologous EST fragments were found in EST databases of *Triticum aestivum*. These fragments overlap; but not to give a complete gene. With reference to the EST sequences found, however, it was possible to generate the Tri a 4-specific primers #199, #203, #204 and #206, which were used for amplification of the Tri a 4 gene from genomic DNA.

In total, 13 clones were analysed.

4 clones were obtained by PCR with primers #204 and #203.

4 clones were obtained by PCR with primers #204 and #199.

3 clones were obtained by PCR with primers #206 and #203.

4 clones were obtained by PCR with primers #206 and #199.

The derived protein sequences begin within the signal sequence of Tri a 4 and extend to the C-terminal end of the protein.

Two variants Tri a 4.01 (from amino acid 22 of SEQ ID NO 8) and Tri a 4.02 (from amino acid 22 of SEQ ID NO 10) were found.

In order to prepare the recombinant allergens according to the invention, the DNA sequences in accordance with SEQ ID NO 1, 3, 5, 7 and 9 were incorporated into expression vectors (for example pProEx, pSE 380). *E. coli*-optimised codons were used for the N-terminal amino acids known from the protein sequencing.

After transformation in *E. coli*, expression and purification of the recombinant allergens according to the invention by various separation techniques, the proteins obtained were subjected to a refolding process. Both allergens can be employed for highly specific diagnosis of grass pollen allergies. This diagnosis can be carried out in vitro by detection of specific antibodies (IgE, IgG1-4, IgA) and reaction with IgE-loaded effector cells (for example basophiles from blood) or in vivo by skin test reactions and provocation at the reaction organ.

The reaction of the allergens according to the invention with T-lymphocytes stimulation of the T-lymphocytes for proliferation and cytokine synthesis both with T-cells in freshly prepared blood lymphocytes and also on established nSec c 4, nHor v 4 or nTri a 4-reactive T-cell lines and clones.

The triplets encoding the cysteines were modified by site-specific mutagenesis in such a way that they encode other amino acids, preferably serine. Both variants in which individual cysteines have been replaced and those in which various combinations of 2 cysteine residues or all cysteines have been modified were prepared. The expressed proteins of these cysteine point mutants have greatly reduced or zero reactivity with IgE antibodies from allergy sufferers, but react with the T-lymphocytes from these patients.

The present invention therefore furthermore relates to a DNA molecule described above or below in which one, a plurality of or all the cysteine residues of the corresponding polypeptide have been replaced with another amino acid by site-specific mutagenesis.

The immunomodulatory activity of hypoallergenic fragments which correspond to polypeptides having T-cell epitopes and that of the hypoallergenic point mutants (for example cysteine replacements) can be detected by their reaction with T-cells from grass pollen allergy sufferers.

Such hypoallergenic fragments or point mutants of the cysteines can be employed as preparations for hyposensitisation of allergy sufferers since they react with the T-cells with equal effectiveness, but result in reduced IgE-mediated side effects owing to the reduced or entirely absent IgE reactivity.

If the nucleic acids encoding the hypoallergenic allergen variants according to the Invention or the unmodified DNA molecules according to the invention are ligated with a human expression vector, these constructs can likewise be used as preparations for immunotherapy (DNA vaccination).

Finally, the present invention relates to pharmaceutical compositions comprising at least one DNA molecule described above or at least one expression vector described above and optionally further active ingredients and/or adjuvants for the immunotherapeutic DNA vaccination of patients with allergies in the triggering of which group 4 allergens from the *Poaceae*, preferably *Triticeae*, in particular Sec c 4, Hor v 4, Tri a 4, are involved and/or for the prevention of such allergies.

A further group of pharmaceutical compositions according to the invention comprises at least one polypeptide described above instead of the DNA and is suitable for the diagnosis and/or treatment of said allergies.

Pharmaceutical compositions in the sense of the present invention comprise, as active ingredients, a polypeptide according to the invention or an expression vector and/or respective pharmaceutically usable derivatives thereof, including mixtures thereof in all ratios. The active ingredients according to the invention can be brought into a suitable dosage form here together with at least one solid, liquid and/or semi-liquid excipient or adjuvant and optionally in combination with one or more further active ingredients.

Particularly suitable adjuvants are immunostimulatory DNA or oligonucleotides having CpG motives.

These compositions can be used as therapeutic agents or diagnostic agents in human or veterinary medicine. Suitable excipients are organic or inorganic substances which are suitable for parenteral administration and do not adversely affect the action of the active ingredient according to the invention. Suitable for parenteral use are, in particular, solutions, preferably oil-based or aqueous solutions, furthermore suspensions, emulsions or implants. The active ingredient according to the invention may also be lyophilised and the resultant lyophilisates used, for example, for the preparation of injection preparations. The compositions indicated may be sterilised and/or comprise adjuvants, such as preservatives, stabilisers and/or wetting agents, emulsifiers, salts for modifying the osmotic pressure, buffer substances and/or a plurality of further active ingredients.

Furthermore, sustained-release preparations can be obtained by corresponding formulation of the active ingredient according to the invention—for example by adsorption on aluminium hydroxide.

The invention thus also serves for improving in vitro diagnosis as part of allergen component-triggering identification of the patient-specific sensitisation spectrum. The invention likewise serves for the preparation of significantly improved preparations for the specific immunotherapy of grass pollen allergies.

TABLE 1

Primers used

| Primer number | SEQ ID NO | Sequence |
|---|---|---|
| a) Sec c 4 | | |
| #0083 | 30 | GGCTCCCGGGGCGAACCAGTAG |
| #0087 | 31 | ACCAACGCCTCCCACATCCAGTC |
| #0189 | 32 | GATAAGCTTCTCGAGTGATTAGTACT TTTTGATCAGCGGCGGGATGCTC |
| #0195 | 33 | GCTCTCGATCGGCTACAATGGCG |
| #0198 | 34 | CACGCACTACAAATCICCATGCAAG |
| #0202 | 35 | CATGCTTGATCCTTATTCTACTAGTT GGGC |
| #0203 | 36 | TACGCACGATCCTTATTCTACTAGTT GGGC |
| a) Hor v 4 | | |
| #0194 | 37 | GCCTTGTCCTGCCACCACGCCGCCGC CACC |
| #0195 | 38 | GCTCTCGATCGGCTACAATGGCG |
| #0198 | 39 | CACGCACTACAAATCTCCATGCAAG |
| #0202 | 40 | CATGCTTGATCCTTATTCTACTAGTT GGGC |
| c) Tri a 4 | | |
| #0199 | 41 | CACGCACTAAATCTCCATGCAAG |
| #0203 | 42 | TACGCACGATCCTTATTCTACTAGTT GGGC |
| #0204 | 43 | AAGCTCTATCGCCTACAATGGCG |
| #0206 | 44 | GGTGCTCCTCTTCTGCGCCTTGTCC |

We claim:

1. An isolated polypeptide which is
   (a) a polypeptide consisting of amino acids 23 to 518 of SEQ ID NO: 2;
   (d) a polypeptide consisting of amino acids 23 to 520 of SEQ ID NO: 4;
   (c) a polypeptide consisting of amino acids 23 to 518 of SEQ ID NO: 6;
   (d) a polypeptide consisting of amino acids 22 to 518 of SEQ ID NO: 8; or
   (j) a polypeptide consisting of amino acids 22 to 518 of SEQ ID NO: 10.

2. The polypeptide according to claim 1, which is a recombinant polypeptide.

3. A medicament comprising at least one polypeptide according to claim 1 and a carrier.

4. A pharmaceutical composition comprising at least one polypeptide according to claims 1 and another active ingredient or an adjuvant.

* * * * *